(12) United States Patent
Saris et al.

(10) Patent No.: US 8,911,730 B2
(45) Date of Patent: *Dec. 16, 2014

(54) METHODS OF USING ANTIBODIES TO BLOCK HUMAN THYMIC STROMAL LYMPHOPOIETIN (TSLP) RECEPTOR ACTIVITY

(71) Applicant: Amgen Inc., Thousand Oaks, CA (US)

(72) Inventors: Chris Saris, Newbury Park, CA (US); Ming-Shi Chang, Tainan (TW)

(73) Assignee: Amgen Inc., Thousand Oaks, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 13/690,799

(22) Filed: Nov. 30, 2012

(65) Prior Publication Data

US 2013/0084290 A1    Apr. 4, 2013

Related U.S. Application Data

(63) Continuation of application No. 13/156,106, filed on Jun. 8, 2011, now Pat. No. 8,344,110, which is a continuation of application No. 09/895,943, filed on Jun. 28, 2001, now Pat. No. 7,964,713.

(60) Provisional application No. 60/214,866, filed on Jun. 28, 2000.

(51) Int. Cl.
- *A61K 39/00* (2006.01)
- *C07K 16/28* (2006.01)
- *C07K 14/715* (2006.01)

(52) U.S. Cl.
CPC ....... *C07K 16/2866* (2013.01); *C12N 2799/021* (2013.01); *C07K 14/715* (2013.01); *C07K 14/7155* (2013.01); *C07K 2319/00* (2013.01); *A01K 2217/05* (2013.01)
USPC ..................................... 424/139.1; 424/133.1

(58) Field of Classification Search
None
See application file for complete search history.

(56) References Cited

U.S. PATENT DOCUMENTS 6,844,170 B1    1/2005 Moore et al.

OTHER PUBLICATIONS

Bazan, Haemopoietic receptors and helical cytokines, Immunol Today 11:350-354, 1990.
Bork et al., Go hunting in sequence databases but watch out for the traps, Trends Genet 12:425-427, 1996.
Bork, Powers and pitfalls in sequence analysis: the 70% hurdle, Genome Res 10:398-400, 2000.
Brenner, Errors in genome annotation, Trends Genet 15:132-133, 1999.
Burdach et al., The physiologic role of interleukin-3, interleukin-5, granulocyte-macrophage colony-stimulating factor, and the Bc receptor system, Curr Opin Hematol 5:177-180,1998.
Candeias et al., Defective T-cell receptor y gene rearrangement in interleukin-7 receptor knockout mice, Immunity 6:501-508, 1997.
Candeias et al., IL-7 receptor and VDJ recombination: trophic versus mechanistic actions, Immunol Left 57:9-14, 1997.
Cao et al., Characterization of cDNAs encoding the murine interleukin 2 receptor (IL-2R) y chain: chromosomal mapping and tissue specificity of IL-2R y chain expression, Proc Natl Acad Sci USA 90:8464-8468, 1993.
Database EMBL Online Accession No. AB031333, Feb. 24, 2000, Kitamura and Fujio: *Mus musculus* mRNA for cytokine receptor deltal, complete cds XP002193897.
Database EMBL Online Accession No. AB039945, Mar. 14, 2000, Hiroyama et al., *Mus musculus* CRLM2 mRNA for cytokine receptor like molecule 2, complete cds.
Doerks et al., Protein annotation: detective work for function prediction, Trends Genet 14:248-250, 1998.
Friend et al., A thymic stromal call line supports in vitro development of surface IgM+ B cells and produces a novel growth factor affecting B and T lineage cells, Exp. Hematol. 22(3): 321 328, 1994.
Fujio et al., Molecular cloning of a novel type I cytokine receptor similar to the common gamma chain, Blood 95 (7):2204-2211,2000.
Giri et al., Utilization of the B and y chains of the IL-2 receptor by the novel cytokine IL-15, EMBO J 13:2822-2830, 1994.
Guthridge et al., Mechanism of activation of the GM-CSF, IL-3, and IL-5 family of receptors, Stem Cells 16:301-313, 1998.
He et al., The common Y-chain of cytokine receptors regulates intrathymic T cell development at multiple states, J Immunol 158:2592-2599,1997.
Hirano et al., Signaling mechanisms through gp130: a model of the cytokine system, Cytokine Growth Factor Rev 8:241-252,1997.
Hiroyama Takashi et al., Molecular cloning and characterization of CRLM-2, a novel type I cytokine receptor preferentially expressed in hematopoietic cells, Biochem Biophys Res Commun 272 (1):224-229,2000.
Isaksen et al., Requirement for stat5 in thymic stromal lymphopoietin-mediated signal transduction, J Immunol 163 (11):5971-5977, 1999.
Kimura et al., Sharing of the IL-2 receptor Y chain with the functional IL-9 receptor complex, Int Immunol 7:115-120, 1995.
Kobayashi et al., Cloning and sequencing of the cDNA encoding a mouse IL-2 receptor Y, Gene 130:303-304, 1993.
Kondo et al., Functional participation of the IL-2 receptor Y chain in IL-7 receptor complexes, Science 263:1453-1454, 1994.

(Continued)

*Primary Examiner* — Robert Landsman
(74) *Attorney, Agent, or Firm* — Marshall, Gerstein & Borun LLP

(57) ABSTRACT

The present invention provides Thymic Stromal Lymphopoietin Receptor (TSLPR) polypeptides and nucleic acid molecules encoding the same. The invention also provides selective binding agents, vectors, host cells, and methods for producing TSLPR polypeptides. The invention further provides pharmaceutical compositions and methods for the diagnosis, treatment, amelioration, and/or prevention of diseases, disorders, and conditions associated with TSLPR polypeptides.

6 Claims, 13 Drawing Sheets

(56) References Cited

OTHER PUBLICATIONS

Kondo et al., Sharing of the interleukin-2 (IL-2) receptor Y chain between receptors for IL-2 and IL-4, Science 262:1874-1877, 1993.

Kumaki et al., Cloning of the mouse interleukin-2 receptor Y chain: demonstration of functional differences between the mouse and human receptors, Biochem Biophys Res Commun 193:356-363, 1993.

Lee et al., Normal B cell precursors responsive to recombinant murine IL-7 and inhibition of IL-7 activity by transforming growth factor-B, J Immunol 142:3875-3883,1989.

Leonard et al., JAKS and STATS Biological implications, Annu Rev Immunol 16:293-322, 1998.

Leonard et al., Role of the common cytokine receptor Y chain in cytokine signaling and lymphoid development, Immunol Rev 148:97-114, 1995.

Leonard, Type I cytokines and interferons and their receptors, Fundam Immunol (Paul, ed., Lippincott Raven Publishers 4 Ed.), pp. 741-774, 1999.

Levin et al., Thymic Stromal Lymphopoietin: A cytokine that promotes the development of IgM + B cells in vitro and signals via a novel mechanism, J Immunol 162:677-683, 1999.

Miyajima et al., Signal transduction by the GM-CSF, IL-3 an IL-5 receptors, Leukemia 11:418-422, 1997.

Nelson et al., Cytoplasmic domains of the interleukin-2 receptor B and Y chains mediate the sginal for T-cell proliferation, Nature 369:333-336, 1994.

Noguchi et al., Interleukin-2 receptor Y chain mutation results in X-linked severe combined immunodeficiency in human, Cell 73:147-157, 1993.

Noguchi et al., Interleukin-2 receptor Y chain: a functional component of the interleukin-7 receptor, Science 262:1877-1880, 1993.

Oral Hearing held Jan. 9, 2009 Transcript, Patent Interference No. 105.613.

Park LS, et al., Cloning of the Murine Thymic Stromal Lymphopoietin (TSLP) Receptor: Formation of a Functional Heteromeric Complex Requires Interleukin 7 Receptor, J Experimental Medicine 192(5):659-669, Sep. 2000.

Peschon et al., Early lymphocyte expansion is severely impaired in interleukin 7 receptor mice,J Exp Med 180:1955-1960, 1994.

Rieger et al., Glossary of Genetics, p. 16-17, 1991.

Russell et al., Interaction of IL-2RB and Yc chains with Jak1 and Jak3:implications for XSCID and XCID, Science 266:1042-1045, 1994.

Russell et al., Interleukin-2 receptor Y chain: a functional component of the interleukin-4 receptor, Science 262:1880-1883, 1993.

Skolnick and Fetrow, From genes to protein structure and function: novel applications of computational approaches in the genomic era, Trends Biotechnol 18:34-39, 2000.

Smith and Zhang, The challenges of genome sequence annotation or the devil is in the details, Nat Biotechnol 15:1222-1223, 1997.

Suda et al., A stimulatory effect of recombinant murine interleukin-7 (IL-7) on B-cell colony formation and an inhibitory effect of IL-1a, Blood 74:1936-1941, 1989.

Sudo et al., Interleukin 7 production and function in stromal cell-dependent B cell development, J Exp Med 170:333-338, 1989.

Taga et al., GP130 and the interleukin-6 family of cytokines, Annu Rev Immunol 15:797-819, 1997.

Takeshita et al., Cloning of the Y chain of the human IL-2 receptor, Science 257:379-382, 1992.

von Freeden-Jeffrey et al., Lymphopenia in interleukin (IL)-7 gene-deleted mice identifies IL-7 as a nonredundant cytokine, J Exp Med 181:1519-1526, 1995.

Ziegler et al., Reconstitution of a functional interleukin (IL)-7 receptor demonstrates that the IL-2 receptor Y chain is required for IL-7 signal transduction, Eur J Immunol 25:399-404,1995.

FIG. 1A

```
cccctcctc gccgacccct gaccccgccc cgccccgccc acccagggc ccagacctga   60 gcggcggcca ggtcgcgggt gacgtcacag ggccgttgcc ccatccgtcc cgtggcctgg  120
acggacagag ctgaggcagg ggaataaccg cgagtgctga g atg gca tgg gca ctc 176
                                             Met Ala Trp Ala Leu
                                              1                5
```

| | | | | | | | | | | | | | | | |
|---|---|---|---|---|---|---|---|---|---|---|---|---|---|---|---|
| gcg | gtc | atc | ctc | ctg | cct | cgg | ctc | ctt | gcg | gcg | gca | gcg | gcg | gcg | 224 |
| Ala | Val | Ile | Leu | Leu | Pro | Arg | Leu | Leu | Ala | Ala | Ala | Ala | Ala | Ala | |
| | | | 10 | | | | | 15 | | | | | 20 | | |

| gcg | gtg | acg | tca | cgg | ggt | gat | gtc | aca | gtc | gtc | tgc | cat | gac | ctg | gag | 272 |
|---|---|---|---|---|---|---|---|---|---|---|---|---|---|---|---|---|
| Ala | Val | Thr | Ser | Arg | Gly | Asp | Val | Thr | Val | Val | Cys | His | Asp | Leu | Glu | |
| | | | 25 | | | | | 30 | | | | | 35 | | | |

| acg | gtg | gag | gtc | acg | tgg | ggc | tcg | ggc | ccc | gac | cac | cac | agc | gcc | aac | 320 |
|---|---|---|---|---|---|---|---|---|---|---|---|---|---|---|---|---|
| Thr | Val | Glu | Val | Thr | Trp | Gly | Ser | Gly | Pro | Asp | His | His | Ser | Ala | Asn | |
| | | | 40 | | | | | 45 | | | | | 50 | | | |

| ttg | agc | ctg | gag | ttc | cgt | tat | ggt | act | ggc | gcc | ctg | caa | ccc | tgc | ccg | 368 |
|---|---|---|---|---|---|---|---|---|---|---|---|---|---|---|---|---|
| Leu | Ser | Leu | Glu | Phe | Arg | Tyr | Gly | Thr | Gly | Ala | Leu | Gln | Pro | Cys | Pro | |
| | | 55 | | | | | 60 | | | | | 65 | | | | |

| cga | tat | ttc | ctg | tcc | ggc | gct | ggt | gtc | act | tcc | ggg | tgc | atc | ctc | ccc | 416 |
|---|---|---|---|---|---|---|---|---|---|---|---|---|---|---|---|---|
| Arg | Tyr | Phe | Leu | Ser | Gly | Ala | Gly | Val | Thr | Ser | Gly | Cys | Ile | Leu | Pro | |
| 70 | | | | | 75 | | | | | 80 | | | | | 85 | |

| gcg | gcg | agg | gcg | ggg | ctg | ctg | gag | ctg | gca | ctg | cgc | gac | gga | ggc | ggg | 464 |
|---|---|---|---|---|---|---|---|---|---|---|---|---|---|---|---|---|
| Ala | Ala | Arg | Ala | Gly | Leu | Leu | Glu | Leu | Ala | Leu | Arg | Asp | Gly | Gly | Gly | |
| | | | | 90 | | | | | 95 | | | | | 100 | | |

| gcc | atg | gtg | ttt | aag | gct | agg | cag | cgc | gcg | tcc | gcc | tgg | ctg | aag | ccc | 512 |
|---|---|---|---|---|---|---|---|---|---|---|---|---|---|---|---|---|
| Ala | Met | Val | Phe | Lys | Ala | Arg | Gln | Arg | Ala | Ser | Ala | Trp | Leu | Lys | Pro | |
| | | | 105 | | | | | 110 | | | | | 115 | | | |

| cgc | cca | cct | tgg | aat | gtg | acg | ctg | ctc | tgg | aca | cca | gac | ggg | gac | gtg | 560 |
|---|---|---|---|---|---|---|---|---|---|---|---|---|---|---|---|---|
| Arg | Pro | Pro | Trp | Asn | Val | Thr | Leu | Leu | Trp | Thr | Pro | Asp | Gly | Asp | Val | |
| | | 120 | | | | | 125 | | | | | 130 | | | | |

| act | gtc | tcc | tgg | cct | gcc | cac | tcc | tac | ctg | ggc | ctg | gac | tac | gag | gtg | 608 |
|---|---|---|---|---|---|---|---|---|---|---|---|---|---|---|---|---|
| Thr | Val | Ser | Trp | Pro | Ala | His | Ser | Tyr | Leu | Gly | Leu | Asp | Tyr | Glu | Val | |
| | | 135 | | | | | 140 | | | | | 145 | | | | |

| cag | cac | cgg | gag | agc | aat | gac | gat | gag | gac | gcc | tgg | cag | acg | acc | tca | 656 |
|---|---|---|---|---|---|---|---|---|---|---|---|---|---|---|---|---|
| Gln | His | Arg | Glu | Ser | Asn | Asp | Asp | Glu | Asp | Ala | Trp | Gln | Thr | Thr | Ser | |
| 150 | | | | | 155 | | | | | 160 | | | | | 165 | |

| ggg | ccc | tgc | tgt | gac | ttg | aca | gtg | ggc | ggg | ctc | gac | ccc | gcg | cgc | tgc | 704 |
|---|---|---|---|---|---|---|---|---|---|---|---|---|---|---|---|---|
| Gly | Pro | Cys | Cys | Asp | Leu | Thr | Val | Gly | Gly | Leu | Asp | Pro | Ala | Arg | Cys | |
| | | | | 170 | | | | | 175 | | | | | 180 | | |

FIG. 1B

```
tat gac ttc cgg gtt cgg gcg tcg ccc cgg gcc gcg cac tat ggc ctg    752
Tyr Asp Phe Arg Val Arg Ala Ser Pro Arg Ala Ala His Tyr Gly Leu
            185                 190                 195 gag gcg cag cct agc gag tgg aca gcg gtg aca agg ctt tcc ggg gca    800
Glu Ala Gln Pro Ser Glu Trp Thr Ala Val Thr Arg Leu Ser Gly Ala
        200                 205                 210 gca tcc gcg ggt gac ccc tgc gcc gcc cac ctt ccc ccc cta gcc tcc    848
Ala Ser Ala Gly Asp Pro Cys Ala Ala His Leu Pro Pro Leu Ala Ser
        215                 220                 225 tgt acc gca agc ccc gcc cca tcc ccg gcc ctg gcc ccg ccc ctc ctg    896
Cys Thr Ala Ser Pro Ala Pro Ser Pro Ala Leu Ala Pro Pro Leu Leu
230                 235                 240                 245 ccc ctg ggc tgc ggc cta gca gcg ctg ctg aca ctg tcc ctg ctc ctg    944
Pro Leu Gly Cys Gly Leu Ala Ala Leu Leu Thr Leu Ser Leu Leu Leu
            250                 255                 260 gcc gcc ctg agg ctt cgc agg gtg aaa gat gcg ctg ctg ccc tgc gtc    992
Ala Ala Leu Arg Leu Arg Arg Val Lys Asp Ala Leu Leu Pro Cys Val
        265                 270                 275 cct gac ccc agc ggc tcc ttc cct gga ctc ttt gag aag cat cac ggg   1040
Pro Asp Pro Ser Gly Ser Phe Pro Gly Leu Phe Glu Lys His His Gly
        280                 285                 290 aac ttc cag gcc tgg att gcg gac gcc cag gcc aca gcc ccg cca gcc   1088
Asn Phe Gln Ala Trp Ile Ala Asp Ala Gln Ala Thr Ala Pro Pro Ala
        295                 300                 305 agg acc gag gag gaa gat gac ctc atc cac ccc aag gct aag agg gtg   1136
Arg Thr Glu Glu Glu Asp Asp Leu Ile His Pro Lys Ala Lys Arg Val
310                 315                 320                 325 gag ccc gag gat ggc acc tcc ctc tgc acc gtg cca agg cca ccc agc   1184
Glu Pro Glu Asp Gly Thr Ser Leu Cys Thr Val Pro Arg Pro Pro Ser
            330                 335                 340 ttc gag cca agg ggg ccg gga ggc ggg gcc atg gtg tca gtg ggc ggg   1232
Phe Glu Pro Arg Gly Pro Gly Gly Gly Ala Met Val Ser Val Gly Gly
            345                 350                 355 gcc acg ttc atg gtg ggc gac agc ggc tac atg acc ctg tga           1274
Ala Thr Phe Met Val Gly Asp Ser Gly Tyr Met Thr Leu
            360                 365                 370 ccttgaagtc actgccagtc tatacttcag gctgaggtca cttcctgtct ttaaataatt 1334 caaactcaca aatcctgtgc ctgtctgtat gcaaatgtgg tcacgaatat tcaaataaaa 1394 tgcaaatgct atgct                                                  1409
```

| | | | | | | | | | | | | | | | | |
|---|---|---|---|---|---|---|---|---|---|---|---|---|---|---|---|---|
| atg | ggg | cgg | ctg | gtt | ctg | ctg | tgg | gga | gct | gcc | gtc | ttt | ctg | ctg | gga | 48 |
| Met | Gly | Arg | Leu | Val | Leu | Leu | Trp | Gly | Ala | Ala | Val | Phe | Leu | Leu | Gly | |
| 1 | | | | 5 | | | | | 10 | | | | | 15 | | |
| ggc | tgg | atg | gct | ttg | ggg | caa | gga | gga | gca | gca | gaa | gga | gta | cag | att | 96 |
| Gly | Trp | Met | Ala | Leu | Gly | Gln | Gly | Gly | Ala | Ala | Glu | Gly | Val | Gln | Ile | |
| | | | 20 | | | | | 25 | | | | | 30 | | | |
| cag | atc | atc | tac | ttc | aat | tta | gaa | acc | gtg | cag | gtg | aca | tgg | aat | gcc | 144 |
| Gln | Ile | Ile | Tyr | Phe | Asn | Leu | Glu | Thr | Val | Gln | Val | Thr | Trp | Asn | Ala | |
| | | 35 | | | | | 40 | | | | | 45 | | | | |
| agc | aaa | tac | tcc | agg | acc | aac | ctg | act | ttc | cac | tac | aga | ttc | aac | ggt | 192 |
| Ser | Lys | Tyr | Ser | Arg | Thr | Asn | Leu | Thr | Phe | His | Tyr | Arg | Phe | Asn | Gly | |
| | 50 | | | | | 55 | | | | | 60 | | | | | |
| gat | gag | gcc | tat | gac | cag | tgc | acc | aac | tac | ctt | ctc | cag | gaa | ggt | cac | 240 |
| Asp | Glu | Ala | Tyr | Asp | Gln | Cys | Thr | Asn | Tyr | Leu | Leu | Gln | Glu | Gly | His | |
| 65 | | | | | 70 | | | | | 75 | | | | | 80 | |
| act | tca | ggg | tgc | ctc | cta | gac | gca | gag | cag | cga | gac | gac | att | ctc | tat | 288 |
| Thr | Ser | Gly | Cys | Leu | Leu | Asp | Ala | Glu | Gln | Arg | Asp | Asp | Ile | Leu | Tyr | |
| | | | | 85 | | | | | 90 | | | | | 95 | | |
| ttc | tcc | atc | agg | aat | ggg | acg | cac | ccc | gtt | ttc | acc | gca | agt | cgc | tgg | 336 |
| Phe | Ser | Ile | Arg | Asn | Gly | Thr | His | Pro | Val | Phe | Thr | Ala | Ser | Arg | Trp | |
| | | | 100 | | | | | 105 | | | | | 110 | | | |
| atg | gtt | tat | tac | ctg | aaa | ccc | agt | tcc | ccg | aag | cac | gtg | aga | ttt | tcg | 384 |
| Met | Val | Tyr | Tyr | Leu | Lys | Pro | Ser | Ser | Pro | Lys | His | Val | Arg | Phe | Ser | |
| | | | 115 | | | | | 120 | | | | | 125 | | | |
| tgg | cat | cag | gat | gca | gtg | acg | gtg | acg | tgt | tct | gac | ctg | tcc | tac | ggg | 432 |
| Trp | His | Gln | Asp | Ala | Val | Thr | Val | Thr | Cys | Ser | Asp | Leu | Ser | Tyr | Gly | |
| | | 130 | | | | | 135 | | | | | 140 | | | | |
| gat | ctc | ctc | tat | gag | gtt | cag | tac | cgg | agc | ccc | ttc | gac | acc | gag | tgg | 480 |
| Asp | Leu | Leu | Tyr | Glu | Val | Gln | Tyr | Arg | Ser | Pro | Phe | Asp | Thr | Glu | Trp | |
| 145 | | | | | 150 | | | | | 155 | | | | | 160 | |
| cag | tcc | aaa | cag | gaa | aat | acc | tgc | aac | gtc | acc | ata | gaa | ggc | ttg | gat | 528 |
| Gln | Ser | Lys | Gln | Glu | Asn | Thr | Cys | Asn | Val | Thr | Ile | Glu | Gly | Leu | Asp | |
| | | | | 165 | | | | | 170 | | | | | 175 | | |
| gcc | gag | aag | tgt | tac | tct | ttc | tgg | gtc | agg | gtg | aag | gct | atg | gag | gat | 576 |
| Ala | Glu | Lys | Cys | Tyr | Ser | Phe | Trp | Val | Arg | Val | Lys | Ala | Met | Glu | Asp | |
| | | | | 180 | | | | | 185 | | | | | 190 | | |
| gta | tat | ggg | cca | gac | aca | tac | cca | agc | gac | tgg | tca | gag | gtg | aca | tgc | 624 |
| Val | Tyr | Gly | Pro | Asp | Thr | Tyr | Pro | Ser | Asp | Trp | Ser | Glu | Val | Thr | Cys | |
| | | 195 | | | | | 200 | | | | | 205 | | | | |

FIG. 3B

```
tgg cag aga ggc gag att cgg gat gcc tgt gca gag aca cca acg cct      672
Trp Gln Arg Gly Glu Ile Arg Asp Ala Cys Ala Glu Thr Pro Thr Pro
    210             215             220 ccc aaa cca aag ctg tcc aaa ttt att tta att tcc agc ctg gcc atc      720
Pro Lys Pro Lys Leu Ser Lys Phe Ile Leu Ile Ser Ser Leu Ala Ile
225         230             235             240 ctt ctg atg gtg tct ctc ctc ctt ctg tct tta tgg aaa tta tgg aga      768
Leu Leu Met Val Ser Leu Leu Leu Leu Ser Leu Trp Lys Leu Trp Arg
            245             250             255 gtg aag aag ttt ctc att ccc agc gtg cca gac ccg aaa tcc atc ttc      816
Val Lys Lys Phe Leu Ile Pro Ser Val Pro Asp Pro Lys Ser Ile Phe
                260             265             270 ccc ggg ctc ttt gag ata cac caa ggg aac ttc cag gag tgg atc aca      864
Pro Gly Leu Phe Glu Ile His Gln Gly Asn Phe Gln Glu Trp Ile Thr
        275             280             285 gac acc cag aac gtg gcc cac ctc cac aag atg gca ggt gca gag caa      912
Asp Thr Gln Asn Val Ala His Leu His Lys Met Ala Gly Ala Glu Gln
290         295             300 gaa agt ggc ccc gag gag ccc ctg gta gtc cag ttg gcc aag act gaa      960
Glu Ser Gly Pro Glu Glu Pro Leu Val Val Gln Leu Ala Lys Thr Glu
305             310             315             320 gcc gag tct ccc agg atg ctg gac cca cag acc gag gag aaa gag gcc     1008
Ala Glu Ser Pro Arg Met Leu Asp Pro Gln Thr Glu Glu Lys Glu Ala
                325             330             335 tct ggg gga tcc ctc cag ctt ccc cac cag ccc ctc caa ggc ggt gat     1056
Ser Gly Gly Ser Leu Gln Leu Pro His Gln Pro Leu Gln Gly Gly Asp
        340             345             350 gtg gtc aca atc ggg ggc ttc acc ttt gtg atg aat gac cgc tcc tac     1104
Val Val Thr Ile Gly Gly Phe Thr Phe Val Met Asn Asp Arg Ser Tyr
355             360             365 gtg gcg ttg tga                                                     1116
Val Ala Leu
370
```

FIG. 4A

```
atg ggg cgg ctg gtt ctg ctg tgg gga gct gcc gtc ttt ctg ctg gga    48
Met Gly Arg Leu Val Leu Leu Trp Gly Ala Ala Val Phe Leu Leu Gly
 1               5                  10                 15 ggc tgg atg gct ttg ggg caa gga gga gca gca gaa gga gta cag att    96
Gly Trp Met Ala Leu Gly Gln Gly Gly Ala Ala Glu Gly Val Gln Ile
            20                  25                 30 cag atc atc tac ttc aat tta gaa acc gtg cag gtg aca tgg aat gcc   144
Gln Ile Ile Tyr Phe Asn Leu Glu Thr Val Gln Val Thr Trp Asn Ala
        35                  40                  45 agc aaa tac tcc agg acc aac ctg act ttc cac tac aga ttc aac ggt   192
Ser Lys Tyr Ser Arg Thr Asn Leu Thr Phe His Tyr Arg Phe Asn Gly
    50                  55                  60 gat gag gcc tat gac cag tgc acc aac tac ctt ctc cag gaa ggt cac   240
Asp Glu Ala Tyr Asp Gln Cys Thr Asn Tyr Leu Leu Gln Glu Gly His
65                  70                  75                  80 act tca ggg tgc ctc cta gac gca gag cag cga gac gac att ctc tat   288
Thr Ser Gly Cys Leu Leu Asp Ala Glu Gln Arg Asp Asp Ile Leu Tyr
                85                  90                  95 ttc tcc atc agg aat ggg acg cac ccc gtt ttc acc gca agt cgc tgg   336
Phe Ser Ile Arg Asn Gly Thr His Pro Val Phe Thr Ala Ser Arg Trp
            100                 105                 110 atg gtt tat tac ctg aaa ccc agt tcc ccg aag cac gtg aga ttt tcg   384
Met Val Tyr Tyr Leu Lys Pro Ser Ser Pro Lys His Val Arg Phe Ser
        115                 120                 125 tgg cat cag gat gca gtg acg gtg acg tgt tct gac ctg tcc tac ggg   432
Trp His Gln Asp Ala Val Thr Val Thr Cys Ser Asp Leu Ser Tyr Gly
130                 135                 140 gat ctc ctc tat gag gtt cag tac cgg agc ccc ttc gac acc gag tgg   480
Asp Leu Leu Tyr Glu Val Gln Tyr Arg Ser Pro Phe Asp Thr Glu Trp
145                 150                 155                 160 cag tcc aaa cag gaa aat acc tgc aac gtc acc ata gaa ggc ttg gat   528
Gln Ser Lys Gln Glu Asn Thr Cys Asn Val Thr Ile Glu Gly Leu Asp
                165                 170                 175 gcc gag aag tgt tac tct ttc tgg gtc agg gtg aag gct atg gag gat   576
Ala Glu Lys Cys Tyr Ser Phe Trp Val Arg Val Lys Ala Met Glu Asp
            180                 185                 190 gta tat ggg cca gac aca tac cca agc gac tgg tca gag gtg aca tgc   624
Val Tyr Gly Pro Asp Thr Tyr Pro Ser Asp Trp Ser Glu Val Thr Cys
        195                 200                 205
```

FIG. 4B

```
tgg cag aga ggc gag att cgg gat gcc tgt gca gag aca cca acg cct    672
Trp Gln Arg Gly Glu Ile Arg Asp Ala Cys Ala Glu Thr Pro Thr Pro
    210                 215                 220 ccc aaa cca aag ctg tcc aaa ttt att tta att tcc agc ctg gcc atc    720
Pro Lys Pro Lys Leu Ser Lys Phe Ile Leu Ile Ser Ser Leu Ala Ile
225                 230                 235                 240 ctt ctg atg gtg tct ctc ctc ctt ctg tct tta tgg aaa tta tgg aga    768
Leu Leu Met Val Ser Leu Leu Leu Leu Ser Leu Trp Lys Leu Trp Arg
                245                 250                 255 gtg aag aag ttt ctc att ccc agc gtg cca gac ccg aaa tcc atc ttc    816
Val Lys Lys Phe Leu Ile Pro Ser Val Pro Asp Pro Lys Ser Ile Phe
            260                 265                 270 ccc ggg ctc ttt gag ata cac caa ggg aac ttc cag gag tgg atc aca    864
Pro Gly Leu Phe Glu Ile His Gln Gly Asn Phe Gln Glu Trp Ile Thr
        275                 280                 285 gac acc cag aac gtg gcc cac ctc cac aag atg gca ggt gca gag caa    912
Asp Thr Gln Asn Val Ala His Leu His Lys Met Ala Gly Ala Glu Gln
    290                 295                 300 gaa agt ggc ccc gag gag ccc ctg gta gtc cag ttg gcc aag act gaa    960
Glu Ser Gly Pro Glu Glu Pro Leu Val Val Gln Leu Ala Lys Thr Glu
305                 310                 315                 320 gcc gag tct ccc agg atg ctg gac cca cag acc gag gag aaa gag gcc    1008
Ala Glu Ser Pro Arg Met Leu Asp Pro Gln Thr Glu Glu Lys Glu Ala
                325                 330                 335 tct ggg gga tcc ctc cag ctt ccc cac cag ccc ctc caa ggc ggt gat    1056
Ser Gly Gly Ser Leu Gln Leu Pro His Gln Pro Leu Gln Gly Gly Asp
            340                 345                 350 gtg gtc aca atc ggg ggc ttc acc ttt gtg atg aat gac cgc tcc tac    1104
Val Val Thr Ile Gly Gly Phe Thr Phe Val Met Asn Asp Arg Ser Tyr
        355                 360                 365 gtg gcg ttg gac tac aag gac gac gat gac aag tag                    1140
Val Ala Leu Asp Tyr Lys Asp Asp Asp Asp Lys
    370                 375                 380
```

FIG. 5

```
  1     MAWALAVILLPRLLAAAAAAAAVTSRGDVTVVCHDLETVEVTWGSGPDHH  50
        : |  || ||   :|       ||       : ::  .||||:|||  .     :
  1   MGRLVLLWGAAVFLLGGWMALGQGGAA..EGVQIQIIYFNLETVQVTWNAS.KYS  52

51     SANLSLEFRY.GTGALQPCPRYFLSGAGVTSGCILPA.ARAGLLELALRD  98
        ||.  :|:  |  |    |  ||    ||||:|  |   :|  .:|.
 53     RTNLTFHYRFNGDEAYDQCTNYLLQ.EGHTSGCLLDAEQRDDILYFSIRN 101

99     GGGAMVFKARQRASAWLKPRPPWNVTLLWTPDGDVTVSWPAHSYLGLDYE 148
        |    || |  .    :|||   | .|   |   |    |||.    || | ||
102     GTHP.VFTASRWMVYYLKPSSPKHVRFSWHQDA.VTVTCSDLSYGDLLYE 149

149     VQHRESNDDEDAWQTTSGPCCDLTVGGLDPARCYDFRVRASPRAAHYGLE 198
        ||:|    |   |   ||.         |..|:  |||  :||  |  ||        || :
150     VQYRSPFDTE..WQSKQENTCNVTIEGLDAEKCYSFWVRVKAMEDVYGPD 197

199     AQPSEWTAVTRLSGAASAGDPCAAHLPPLASCTASPAPSPALAPPLLPLG 248
        ||:|.  ||           |  ||            |  .| | | |.    :|
198     TYPSDWSEVTCWQ.RGEIRDACAE........TPTP.PKPKLSKFILT.. 235

249     CGLAALLTLSLLLAAL.RLRRVKDALLPCVPDPSGSFPGLFEKHHGNFQA 297
        ||  ||   .|||| .|  :|   |||    |:| ||||     |||||| |  ||||
236     SSLAILLMVSLLLLSLWKLWRVKKFLIPSVPDPKSIFPGLFEIHQGNFQE 285

298     WIADAQATA...PPARTEEEDDLIHPKAKRVEPEDGTSLCTV.PRPPSFE 343
        || | |  |    |   |:|     |   ..   :   |    . |.         |
286     WITDTQNVAHLHKMAGAEQESGPEEPLVVQLAKTEAESPRMLDPQTEEKE 335

344     ........PRGP.GGGAMVSVGGATFMVGDSGYMTL 370
                |   |  ||  .|.:|| ||..  |  |. |
336     ASGGSLQLPHQPLQGGDVVTIGGFTFVMNDRSYVAL 371
```

METHODS OF USING ANTIBODIES TO BLOCK HUMAN THYMIC STROMAL LYMPHOPOIETIN (TSLP) RECEPTOR ACTIVITY

This application is a continuation of U.S. patent application Ser. No. 13/156,106, filed Jun. 8, 2011, now U. S. Pat. No. 8,344,110, which is a continuation of U.S. patent application Ser. No. 09/895,943, filed on Jun. 28, 2001, now U.S. Pat. No. 7,964,713, which claims the benefit of priority from U.S. Provisional Patent Application No. 60/214,866, filed on Jun. 28, 2000, the disclosure of which is explicitly incorporated by reference herein.

REFERENCE TO THE SEQUENCE LISTING

The present application is being filed along with a Sequence Listing in electronic format. The Sequence Listing is provided as a file entitled A-713-US-CNT2_ST25.txt, created May 23, 2011, which is 46 KB in size. The information in the electronic format of the Sequence Listing is incorporated herein by reference in its entirety.

FIELD OF THE INVENTION

The present invention relates to Thymic Stromal Lymphopoietin Receptor (TSLPR) polypeptides and nucleic acid molecules encoding the same. The invention also relates to selective binding agents, vectors, host cells, and methods for producing TSLPR polypeptides. The invention further relates to pharmaceutical compositions and methods for the diagnosis, treatment, amelioration, and/or prevention of diseases, disorders, and conditions associated with TSLPR polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

Cytokines regulate a variety of cellular responses including proliferation, differentiation, and survival. Among the different classes of cytokines are the type I cytokines, which form four α-helical bundle structures that exhibit an up-up-down-down topology (Bazan, 1990, *Immunol. Today* 11:350-54; Leonard and O'Shea, 1998, *Annu. Rev. Immunol.* 16:293-322; Leonard, *Fundamental Immunology* 741-74 (Paul, ed., Lippincott Raven Publishers 4 ed., 1999)). Type I cytokines include many interleukins, such as IL-2, IL-3, IL-4, IL-5, IL-6, IL-7, IL-9, IL-11, IL-12, IL-13, and IL-15 as well as other hematologically-active molecules such as GM-CSF, erythropoietin, thrombopoietin, and molecules such as growth hormone and prolactin. Signaling by type I cytokines involves interaction with homodimers, heterodimers, or higher order receptor oligomers of the type I cytokine receptor superfamily. Ligand binding induces dimerization or higher order oligomerization, resulting in downstream signaling, in part involving the Jak-STAT pathway (Bazan, supra; Leonard and O'Shea, supra; Leonard, supra).

Thymic stromal lymphopoietin (TSLP) is a cytokine whose biological activities overlap with those of IL-7. For example, both TSLP and IL-7 induce tyrosine phosphorylation of the transcription factor Stat5 (Isaksen et al., 1999, *J. Immunol.* 163:5971-77). TSLP activity was originally identified in the conditioned medium of a thymic stromal cell line that supported the development of murine IgM$^+$ B-cells from fetal liver hematopoietic progenitor cells (Friend et al., 1994 *Exp. Hematol.* 22:321-28). Moreover, TSLP can promote B-cell lymphopoiesis in long-term bone marrow cultures and can co-stimulate both thymocytes and mature T-cells (Friend et al., supra; Levin et al., 1999, *J. Immunol.* 162:677-83). TSLP may also serve as an extrinsic signal to specifically rearrange the T-cell receptor gamma locus (Candeias et al., 1997, *Immunol. Lett.* 57:9-14). Thus, the isolation and characterization of the cytokine receptor for TSLP would allow for the identification of compounds useful in treating TSLP-related diseases or conditions, such as those affecting B-cell development, T-cell development, T-cell receptor gene rearrangement, or regulation of the Stat5 transcription factor.

SUMMARY OF THE INVENTION

The present invention relates to novel TSLPR nucleic acid molecules and encoded polypeptides.

The invention provides for an isolated nucleic acid molecule comprising a nucleotide sequence selected from the group consisting of:

(a) the nucleotide sequence as set forth in any of SEQ ID NO: 1, SEQ ID NO: 4, SEQ ID NO: 7, SEQ ID NO: 10, or SEQ ID NO: 11;

(b) a nucleotide sequence encoding the polypeptide as set forth in any of SEQ ID NO: 2, SEQ ID NO: 5, or SEQ ID NO: 8;

(c) a nucleotide sequence which hybridizes under moderately or highly stringent conditions to the complement of either (b) or (c); and (d) a nucleotide sequence complementary to either (b) or (c).

The invention also provides for an isolated nucleic acid molecule comprising a nucleotide sequence selected from the group consisting of:

(a) a nucleotide sequence encoding a polypeptide which is at least about 70 percent identical to the polypeptide as set forth in any of SEQ ID NO: 2, SEQ ID NO: 5, or SEQ ID NO: 8, wherein the encoded polypeptide has an activity of the polypeptide set forth in any of SEQ ID NO: 2, SEQ ID NO: 5, or SEQ ID NO: 8;

(b) a nucleotide sequence encoding an allelic variant or splice variant of the nucleotide sequence as set forth in any of SEQ ID NO: 1, SEQ ID NO: 4, SEQ ID NO: 7, SEQ ID NO: 10, or SEQ ID NO: 11, or (a);

(c) a region of the nucleotide sequence of any of SEQ ID NO: 1, SEQ ID NO: 4, SEQ ID NO: 7, SEQ ID NO: 10, or SEQ ID NO: 11, (a), or (b) encoding a polypeptide fragment of at least about 25 amino acid residues, wherein the polypeptide fragment has an activity of the polypeptide set forth in any of SEQ ID NO: 2, SEQ ID NO: 5, or SEQ ID NO: 8, or is antigenic;

(d) a region of the nucleotide sequence of any of SEQ ID NO: 1, SEQ ID NO: 4, SEQ ID NO: 7, SEQ ID NO: 10, or SEQ ID NO: 11, or any of (a)-(c) comprising a fragment of at least about 16 nucleotides;

(e) a nucleotide sequence which hybridizes under moderately or highly stringent conditions to the complement of any of (a)-(d); and (f) a nucleotide sequence complementary to any of (a)-(d).

The invention further provides for an isolated nucleic acid molecule comprising a nucleotide sequence selected from the group consisting of:

(a) a nucleotide sequence encoding a polypeptide as set forth in any of SEQ ID NO: 2, SEQ ID NO: 5, or SEQ ID NO: 8 with at least one conservative amino acid substitution, wherein the encoded polypeptide has an activity of the polypeptide set forth in any of SEQ ID NO: 2, SEQ ID NO: 5, or SEQ ID NO: 8;

(b) a nucleotide sequence encoding a polypeptide as set forth in any of SEQ ID NO: 2, SEQ ID NO: 5, or SEQ ID NO: 8 with at least one amino acid insertion, wherein the encoded polypeptide has an activity of the polypeptide set forth in any of SEQ ID NO: 2, SEQ ID NO: 5, or SEQ ID NO: 8;

(c) a nucleotide sequence encoding a polypeptide as set forth in any of SEQ ID NO: 2, SEQ ID NO: 5, or SEQ ID NO: 8 with at least one amino acid deletion, wherein the encoded polypeptide has an activity of the polypeptide set forth in any of SEQ ID NO: 2, SEQ ID NO: 5, or SEQ ID NO: 8;

(d) a nucleotide sequence encoding a polypeptide as set forth in any of SEQ ID NO: 2, SEQ ID NO: 5, or SEQ ID NO: 8 which has a C- and/or N-terminal truncation, wherein the encoded polypeptide has an activity of the polypeptide set forth in any of SEQ ID NO: 2, SEQ ID NO: 5, or SEQ ID NO: 8;

(e) a nucleotide sequence encoding a polypeptide as set forth in any of SEQ ID NO: 2, SEQ ID NO: 5, or SEQ ID NO: 8 with at least one modification selected from the group consisting of amino acid substitutions, amino acid insertions, amino acid deletions, C-terminal truncation, and N-terminal truncation, wherein the encoded polypeptide has an activity of the polypeptide set forth in any of SEQ ID NO: 2, SEQ ID NO: 5, or SEQ ID NO: 8;

(f) a nucleotide sequence of any of (a)-(e) comprising a fragment of at least about 16 nucleotides;

(g) a nucleotide sequence which hybridizes under moderately or highly stringent conditions to the complement of any of (a)-(f); and (h) a nucleotide sequence complementary to any of (a)-(e).

The present invention provides for an isolated polypeptide comprising the amino acid sequence as set forth in any of SEQ ID NO: 2, SEQ ID NO: 5, or SEQ ID NO: 8.

The invention also provides for an isolated polypeptide comprising the amino acid sequence selected from the group consisting of:

(a) the amino acid sequence as set forth in any of SEQ ID NO: 3, SEQ ID NO: 6, or SEQ ID NO: 9, optionally further comprising an amino-terminal methionine;

(b) an amino acid sequence for an ortholog of any of SEQ ID NO: 2, SEQ ID NO: 5, or SEQ ID NO: 8;

(c) an amino acid sequence which is at least about 70 percent identical to the amino acid sequence of any of SEQ ID NO: 2, SEQ ID NO: 5, or SEQ ID NO: 8, wherein the polypeptide has an activity of the polypeptide set forth in any of SEQ ID NO: 2, SEQ ID NO: 5, or SEQ ID NO: 8;

(d) a fragment of the amino acid sequence set forth in any of SEQ ID NO: 2, SEQ ID NO: 5, or SEQ ID NO: 8 comprising at least about 25 amino acid residues, wherein the fragment has an activity of the polypeptide set forth in any of SEQ ID NO: 2, SEQ ID NO: 5, or SEQ ID NO: 8, or is antigenic; and (e) an amino acid sequence for an allelic variant or splice variant of the amino acid sequence as set forth in any of SEQ ID NO: 2, SEQ ID NO: 5, or SEQ ID NO: 8, or any of (a)-(c).

The invention further provides for an isolated polypeptide comprising the amino acid sequence selected from the group consisting of:

(a) the amino acid sequence as set forth in any of SEQ ID NO: 2, SEQ ID NO: 5, or SEQ ID NO: 8 with at least one conservative amino acid substitution, wherein the polypeptide has an activity of the polypeptide set forth in any of SEQ ID NO: 2, SEQ ID NO: 5, or SEQ ID NO: 8;

(b) the amino acid sequence as set forth in any of SEQ ID NO: 2, SEQ ID NO: 5, or SEQ ID NO: 8 with at least one amino acid insertion, wherein the polypeptide has an activity of the polypeptide set forth in any of SEQ ID NO: 2, SEQ ID NO: 5, or SEQ ID NO: 8;

(c) the amino acid sequence as set forth in any of SEQ ID NO: 2, SEQ ID NO: 5, or SEQ ID NO: 8 with at least one amino acid deletion, wherein the polypeptide has an activity of the polypeptide set forth in any of SEQ ID NO: 2, SEQ ID NO: 5, or SEQ ID NO: 8;

(d) the amino acid sequence as set forth in any of SEQ ID NO: 2, SEQ ID NO: 5, or SEQ ID NO: 8 which has a C- and/or N-terminal truncation, wherein the polypeptide has an activity of the polypeptide set forth in any of SEQ ID NO: 2, SEQ ID NO: 5, or SEQ ID NO: 8; and (e) the amino acid sequence as set forth in any of SEQ ID NO: 2, SEQ ID NO: 5, or SEQ ID NO: 8 with at least one modification selected from the group consisting of amino acid substitutions, amino acid insertions, amino acid deletions, C-terminal truncation, and N-terminal truncation, wherein the polypeptide has an activity of the polypeptide set forth in any of SEQ ID NO: 2, SEQ ID NO: 5, or SEQ ID NO: 8.

Also provided are fusion polypeptides comprising TSLPR amino acid sequences.

The present invention also provides for an expression vector comprising the isolated nucleic acid molecules as set forth herein, recombinant host cells comprising the recombinant nucleic acid molecules as set forth herein, and a method of producing a TSLPR polypeptide comprising culturing the host cells and optionally isolating the polypeptide so produced.

A transgenic non-human animal comprising a nucleic acid molecule encoding a TSLPR polypeptide is also encompassed by the invention. The TSLPR nucleic acid molecules are introduced into the animal in a manner that allows expression and increased levels of a TSLPR polypeptide, which may include increased circulating levels. Alternatively, the TSLPR nucleic acid molecules are introduced into the animal in a manner that prevents expression of endogenous TSLPR polypeptide (i.e., generates a transgenic animal possessing a TSLPR polypeptide gene knockout). The transgenic non-human animal is preferably a mammal, and more preferably a rodent, such as a rat or a mouse.

Also provided are derivatives of the TSLPR polypeptides of the present invention.

Additionally provided are selective binding agents such as antibodies and peptides capable of specifically binding the TSLPR polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The TSLPR polypeptides and nucleic acid molecules of the present invention may be used to treat, prevent, ameliorate, and/or detect diseases and disorders, including those recited herein.

The present invention also provides a method of assaying test molecules to identify a test molecule that binds to a TSLPR polypeptide. The method comprises contacting a TSLPR polypeptide with a test molecule to determine the extent of binding of the test molecule to the polypeptide. The method further comprises determining whether such test molecules are agonists or antagonists of a TSLPR polypeptide. The present invention further provides a method of testing the impact of molecules on the expression of TSLPR polypeptide or on the activity of TSLPR polypeptide.

Methods of regulating expression and modulating (i.e., increasing or decreasing) levels of a TSLPR polypeptide are also encompassed by the invention. One method comprises administering to an animal a nucleic acid molecule encoding a TSLPR polypeptide. In another method, a nucleic acid molecule comprising elements that regulate or modulate the expression of a TSLPR polypeptide may be administered. Examples of these methods include gene therapy, cell therapy, and anti-sense therapy as further described herein.

BRIEF DESCRIPTION OF THE FIGURES

FIGS. 1A-1B illustrate the nucleotide sequence of the murine TSLPR gene (SEQ ID NO: 1) and deduced amino acid sequence of murine TSLPR polypeptide (SEQ ID NO: 2). The predicted signal peptide (underline) and transmembrane domain (double underline) are indicated;

FIG. 2 illustrates an amino acid sequence alignment of murine TSLPR polypeptide (upper sequence; SEQ ID NO: 2) and murine common cytokine receptor γ chain ($\gamma_c$) (lower sequence; SEQ ID NO: 12). Identical residues (boxed), potential N-linked glycosylation sites (*), and predicted signal peptide and transmembrane domain (underline) are indicated;

FIGS. 3A-3B illustrate the nucleotide sequence of the human TSLPR gene (SEQ ID NO: 4) and the deduced amino acid sequence of human TSLPR polypeptide (SEQ ID NO: 5). The predicted signal peptide (underline) and transmembrane domain (double underline) are indicated;

FIGS. 4A-4B illustrate the nucleotide sequence of human TSLPR/FLAG (SEQ ID NO: 7) and the deduced amino acid sequence of human TSLPR/FLAG polypeptide (SEQ ID NO: 8). The FLAG peptide (dotted underline), predicted signal peptide (underline), and predicted transmembrane domain (double underline) are indicated;

FIG. 5 illustrates an amino acid sequence alignment of murine TSLPR polypeptide (upper sequence; SEQ ID NO: 2) and human TSLPR polypeptide (lower sequence; SEQ ID NO: 5);

DETAILED DESCRIPTION OF THE INVENTION

Figure 6C:
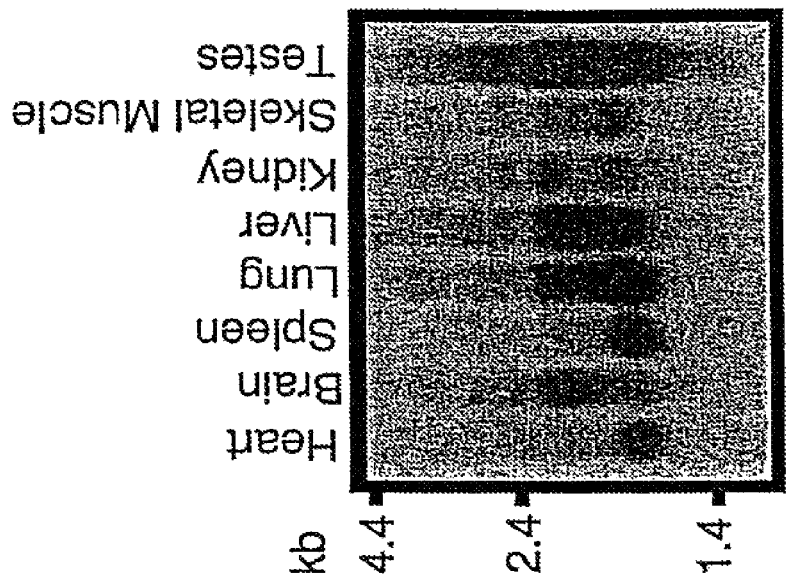
FIGS. 6A-6C illustrate (A) in vitro translation of murine TSLPR polypeptide, (B) immunoprecipitation of murine TSLPR polypeptide from NAG 8/7 cells, and (C) northern blot analysis of murine TSLPR mRNA expression.

The section headings used herein are for organizational purposes only and are not to be construed as limiting the subject matter described. All references cited in this application are expressly incorporated by reference herein.

Definitions

The terms "TSLPR gene" or "TSLPR nucleic acid molecule" or "TSLPR polynucleotide" refer to a nucleic acid molecule comprising or consisting of a nucleotide sequence as set forth in any of SEQ ID NO: 1, SEQ ID NO: 4, SEQ ID NO: 7, SEQ ID NO: 10, or SEQ ID NO: 11, a nucleotide sequence encoding the polypeptide as set forth in any of SEQ ID NO: 2, SEQ ID NO: 5, or SEQ ID NO: 8, and nucleic acid molecules as defined herein.

The term "TSLPR polypeptide allelic variant" refers to one of several possible naturally occurring alternate forms of a gene occupying a given locus on a chromosome of an organism or a population of organisms.

The term "TSLPR polypeptide splice variant" refers to a nucleic acid molecule, usually RNA, which is generated by alternative processing of intron sequences in an RNA transcript of TSLPR polypeptide amino acid sequence as set forth in any of SEQ ID NO: 2, SEQ ID NO: 5, or SEQ ID NO: 8.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "TSLPR polypeptide" refers to a polypeptide comprising the amino acid sequence of any of SEQ ID NO: 2, SEQ ID NO: 5, or SEQ ID NO: 8 and related polypeptides. Related polypeptides include TSLPR polypeptide fragments, TSLPR polypeptide orthologs, TSLPR polypeptide variants, and TSLPR polypeptide derivatives, which possess at least one activity of the polypeptide as set forth in any of SEQ ID NO: 2, SEQ ID NO: 5, or SEQ ID NO: 8. TSLPR polypeptides may be mature polypeptides, as defined herein, and may or may not have an amino-terminal methionine residue, depending on the method by which they are prepared.

The term "TSLPR polypeptide fragment" refers to a polypeptide that comprises a truncation at the amino-terminus (with or without a leader sequence) and/or a truncation at the carboxyl-terminus of the polypeptide as set forth in any of SEQ ID NO: 2, SEQ ID NO: 5, or SEQ ID NO: 8. The term "TSLPR polypeptide fragment" also refers to amino-terminal and/or carboxyl-terminal truncations of TSLPR polypeptide orthologs, TSLPR polypeptide derivatives, or TSLPR polypeptide variants, or to amino-terminal and/or carboxyl-terminal truncations of the polypeptides encoded by TSLPR polypeptide allelic variants or TSLPR polypeptide splice variants. TSLPR polypeptide fragments may result from alternative RNA splicing or from in vivo protease activity. Membrane-bound forms of a TSLPR polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such TSLPR polypeptide fragments may optionally comprise an amino-terminal methionine residue. It will be appreciated that such fragments can be used, for example, to generate antibodies to TSLPR polypeptides.

The term "TSLPR polypeptide ortholog" refers to a polypeptide from another species that corresponds to TSLPR polypeptide amino acid sequence as set forth in any of SEQ ID NO: 2, SEQ ID NO: 5, or SEQ ID NO: 8. For example, mouse and human TSLPR polypeptides are considered orthologs of each other.

The term "TSLPR polypeptide variants" refers to TSLPR polypeptides comprising ammo acid sequences having one or more amino acid sequence substitutions, deletions (such as internal deletions and/or TSLPR polypeptide fragments), and/or additions (such as internal additions and/or TSLPR fusion polypeptides) as compared to the TSLPR polypeptide amino acid sequence set forth in any of SEQ ID NO: 2, SEQ ID NO: 5, or SEQ ID NO: 8 (with or without a leader sequence). Variants may be naturally occurring (e.g., TSLPR polypeptide allelic variants, TSLPR polypeptide orthologs, and TSLPR polypeptide splice variants) or artificially constructed. Such TSLPR polypeptide variants may be prepared from the corresponding nucleic acid molecules having a DNA sequence that varies accordingly from the DNA sequence as set forth in any of SEQ ID NO: 1, SEQ ID NO: 4, SEQ ID NO: 7, SEQ ID NO: 10, or SEQ ID NO: 11. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "TSLPR polypeptide derivatives" refers to the polypeptide as set forth in any of SEQ ID NO: 2, SEQ ID NO: 5, or SEQ ID NO: 8, TSLPR polypeptide fragments, TSLPR polypeptide orthologs, or TSLPR polypeptide variants, as defined herein, that have been chemically modified. The term "TSLPR polypeptide derivatives" also refers to the polypeptides encoded by TSLPR polypeptide allelic variants or TSLPR polypeptide splice variants, as defined herein, that have been chemically modified.

The term "mature TSLPR polypeptide" refers to a TSLPR polypeptide lacking a leader sequence. A mature TSLPR polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like. Exemplary mature TSLPR polypeptides are depicted by the amino acid sequences as set forth in SEQ ID NO: 3, SEQ ID NO: 6, and SEQ ID NO: 9.

The term "TSLPR fusion polypeptide" refers to a fusion of one or more amino acids (such as a heterologous protein or peptide) at the amino- or carboxyl-terminus of the polypeptide as set forth in any of SEQ ID NO: 2, SEQ ID NO: 5, or SEQ ID NO: 8, TSLPR polypeptide fragments, TSLPR polypeptide orthologs, TSLPR polypeptide variants, or TSLPR derivatives, as defined herein. The term "TSLPR fusion polypeptide" also refers to a fusion of one or more amino acids at the amino- or carboxyl-terminus of the polypeptide encoded by TSLPR polypeptide allelic variants or TSLPR polypeptide splice variants, as defined herein.

The term "biologically active TSLPR polypeptides" refers to TSLPR polypeptides having at least one activity characteristic of the polypeptide comprising the amino acid sequence of any of SEQ ID NO: 2, SEQ ID NO: 5, or SEQ ID NO: 8. In addition, a TSLPR polypeptide may be active as an immunogen; that is, the TSLPR polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of a TSLPR polypeptide or TSLPR nucleic acid molecule used to support an observable level of one or more biological activities of the TSLPR polypeptides as set forth herein.

The term "pharmaceutically acceptable carrier" or "physiologically acceptable carrier" as used herein refers to one or more formulation materials suitable for accomplishing or enhancing the delivery of the TSLPR polypeptide, TSLPR nucleic acid molecule, or TSLPR selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a TSLPR polypeptide. As used herein, the terms, "specific" and "specificity" refer to the ability of the selective binding agents to bind to human TSLPR polypeptides and not to bind to human non-TSLPR polypeptides. It will be appreciated, however, that the selective binding agents may also bind orthologs of the polypeptide as set forth in any of SEQ ID NO: 2, SEQ ID NO: 5, or SEQ ID NO: 8, that is, interspecies versions thereof, such as mouse and rat TSLPR polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of any of SEQ ID NO: 1, SEQ ID NO: 4, SEQ ID NO: 7, SEQ ID NO: 10, or SEQ ID NO: 11, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide as set forth in any of SEQ ID NO: 2, SEQ ID NO: 5, or SEQ ID NO: 8. Such related TSLPR polypeptides may comprise, for example, an addition and/or a deletion of one or more N linked or O-linked glycosylation sites or an addition and/or a deletion of one or more cysteine residues.

Related nucleic acid molecules also include fragments of TSLPR nucleic acid molecules which encode a polypeptide of at least about 25 contiguous amino acids, or about 50 amino acids, or about 75 amino acids, or about 100 amino acids, or about 150 amino acids, or about 200 amino acids, or more than 200 amino acid residues of the TSLPR polypeptide of any of SEQ ID NO: 2, SEQ ID NO: 5, or SEQ ID NO: 8.

In addition, related TSLPR nucleic acid molecules also include those molecules which comprise nucleotide sequences which hybridize under moderately or highly stringent conditions as defined herein with the fully complementary sequence of the TSLPR nucleic acid molecule of any of SEQ ID NO: 1, SEQ ID NO: 4, SEQ ID NO: 7, SEQ ID NO: 10, or SEQ ID NO: 11, or of a molecule encoding a polypeptide, which polypeptide comprises the amino acid sequence as shown in any of SEQ ID NO: 2, SEQ ID NO: 5, or SEQ ID NO: 8, or of a nucleic acid fragment as defined herein, or of a nucleic acid fragment encoding a polypeptide as defined herein. Hybridization probes may be prepared using the TSLPR sequences provided herein to screen cDNA, genomic or synthetic DNA libraries for related sequences. Regions of the DNA and/or amino acid sequence of TSLPR polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinylpyrrolidone 0.1% sodium pyrophosphate, 0.1% sodium dodecylsutfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log[Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

* The sodium ion concentration in 6× salt sodium citrate (SSC) is 1M. See Suggs et al., *Developmental Biology Using Purified Genes* 683 (Brown and Fox, eds., 1981).

Tm=2° C. per A-T base pair+4° C. per G-C base pair

High stringency washing conditions for oligonucleotides are usually at a temperature of 0-5° C. below the Tm of the oligonucleotide in 6×SSC, 0.1% SDS, In another embodiment, related nucleic acid molecules comprise or consist of a nucleotide sequence that is at least about 70 percent identical to the nucleotide sequence as shown in any of SEQ ID NO: 1, SEQ ID NO: 4, SEQ ID NO: 7, SEQ ID NO: 10, or SEQ ID NO: 11, or comprise or consist essentially of a nucleotide sequence encoding a polypeptide that is at least about 70 percent identical to the polypeptide as set forth in any of SEQ ID NO: 2, SEQ ID NO: 5, or SEQ ID NO: 8. In preferred embodiments, the nucleotide sequences are about 75 percent, or about 80 percent, or about 85 percent, or about 90 percent, or about 95, 96, 97, 98, or 99 percent identical to the nucleotide sequence as shown in any of SEQ ID NO: 1, SEQ ID NO: 4, SEQ ID NO: 7, SEQ ID NO: 10, or SEQ ID NO: 11, or the nucleotide sequences encode a polypeptide that is about 75 percent, or about 80 percent, or about 85 percent, or about 90 percent, or about 95, 96, 97, 98, or 99 percent identical to the polypeptide sequence as set forth in any of SEQ ID NO: 2, SEQ ID NO: 5, or SEQ ID NO: 8. Related nucleic acid molecules encode polypeptides possessing at least one activity of the polypeptide set forth in any of SEQ ID NO: 2, SEQ ID NO: 5, or SEQ ID NO: 8.

Differences in the nucleic acid sequence may result in conservative and/or non-conservative modifications of the amino acid sequence relative to the amino acid sequence of any of SEQ ID NO: 2, SEQ ID NO: 5, or SEQ ID NO: 8.

Conservative modifications to the amino acid sequence of any of SEQ ID NO: 2, SEQ ID NO: 5, or SEQ ID NO: 8 (and the corresponding modifications to the encoding nucleotides) will produce a polypeptide having functional and chemical characteristics similar to those of TSLPR polypeptides. In contrast, substantial modifications in the functional and/or chemical characteristics of TSLPR polypeptides may be accomplished by selecting substitutions in the amino acid sequence of any of SEQ ID NO: 2, SEQ ID NO: 5, or SEQ ID NO: 8 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
   1) hydrophobic: norleucine, Met, Ala, Val, Leu, Ile;
   2) neutral hydrophilic: Cys, Ser, Thr;
   3) acidic: Asp, Glu;
   4) basic: Asn, Gln, His, Lys, Arg;
   5) residues that influence chain orientation: Gly, Pro; and
   6) aromatic: Trp, Tyr, Phe.

For example, non-conservative substitutions may involve the exchange of a member of one of these classes for a member from another class. Such substituted residues may be introduced into regions of the human TSLPR polypeptide that are homologous with non-human TSLPR polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the TSLPR polypeptide, or to increase or decrease the affinity of the TSLPR polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NO: 2, SEQ ID NO: 5, or SEQ ID NO: 8 using well-known techniques. For identifying suitable areas of the molecule that may be changed without destroying biological activity, one skilled in die art may target areas not believed to be important for activity. For example, when similar polypeptides with similar activities from the same species or from other species are known, one skilled in the art may compare the amino acid sequence of a TSLPR polypeptide to such similar polypeptides. With such a comparison, one can identity residues and portions of the molecules that are conserved among similar polypeptides. It will be appreciated that changes in areas of the TSLPR molecule that are not conserved relative to such similar polypeptides would be less likely to adversely affect the biological activity and/or structure of a TSLPR polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a TSLPR polypeptide that correspond to amino acid residues that are important for activity or structure in similar polypeptides. One skilled in the art may opt for chemically similar amino acid substitutions for such predicted important amino acid residues of TSLPR polypeptides.

One skilled in the art can also analyze the three-dimensional structure and amino acid sequence in relation to that structure in similar polypeptides. In view of such information, one skilled in the art may predict the alignment of amino acid residues of TSLPR polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997. *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990. *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred TSLPR polypeptide variants include glycosylation variants wherein the number and/or type of glycosylation sites have been altered compared to the amino acid sequence set forth in any of SEQ ID NO: 2, SEQ ID NO: 5, or SEQ ID NO: 8. In one embodiment, TSLPR polypeptide variants comprise a greater or a lesser number of N-linked glycosylation sites than the amino acid sequence set forth in any of SEQ ID NO: 2, SEQ ID NO: 5, or SEQ ID NO: 8. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred TSLPR variants include cysteine variants, wherein one or more cysteine residues are deleted or substituted with another amino acid (e.g., serine) as compared to the amino acid sequence set forth in any of SEQ ID NO: 2, SEQ ID NO: 5, or SEQ ID NO: 8. Cysteine variants are useful when TSLPR polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in any of SEQ ID NO: 2, SEQ ID NO: 5, or SEQ ID NO: 8 with at least one amino acid insertion and wherein the polypeptide has an activity of the polypeptide set forth in any of SEQ ID NO: 2, SEQ ID NO: 5, or SEQ ID NO: 8, or a nucleotide sequence encoding a polypeptide as set forth in any of SEQ ID NO: 2, SEQ ID NO: 5, or SEQ ID NO: 8 with at least one amino acid deletion and wherein the polypeptide has an activity of the polypeptide set forth in any of SEQ ID NO: 2, SEQ ID NO: 5, or SEQ ID NO: 8. Related nucleic acid molecules also comprise or consist of a nucleotide sequence encoding a polypeptide as set forth in any of SEQ ID NO: 2, SEQ ID NO: 5, or SEQ ID NO: 8 wherein the polypeptide has a carboxyl- and/or amino-terminal truncation and further wherein the polypeptide has an activity of the polypeptide set forth in any of SEQ ID NO: 2, SEQ ID NO: 5, or SEQ ID NO: 8. Related nucleic acid molecules also comprise or consist of a nucleotide sequence encoding a polypeptide as set forth in any of SEQ ID NO: 2, SEQ ID NO: 5, or SEQ ID NO: 8 with at least one modification selected from the group consisting of amino acid substitutions, amino acid insertions, amino acid deletions, carboxyl-terminal truncations, and amino-terminal truncations and wherein the polypeptide has an activity of the polypeptide set forth in any of SEQ ID NO: 2, SEQ ID NO: 5, or SEQ ID NO: 8.

In addition, the polypeptide comprising the amino acid sequence of any of SEQ ID NO: 2, SEQ ID NO: 5, or SEQ ID NO: 8, or other TSLPR polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a TSLPR fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in any of SEQ ID NO: 2, SEQ ID NO: 5, or SEQ ID NO: 8, or other TSLPR polypeptide.

Fusions can be made either at the amino-terminus or at the carboxyl-terminus of the polypeptide comprising the amino acid sequence set forth in any of SEQ ID NO: 2, SEQ ID NO: 5, or SEQ ID NO: 8, or other TSLPR polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of any of SEQ ID NO: 2, SEQ ID NO: 5, or SEQ ID NO: 8, or other TSLPR polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

and CH3 region may be fused at either the amino-terminus or carboxyl-terminus of a TSLPR polypeptide fragment (e.g., the predicted extracellular portion of TSLPR polypeptide).

The resulting TSLPR fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides are readily calculated by known methods. Such methods include, but are not limited to those described in *Computational Molecular Biology* (A. M. Lesk. ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); Sequence Analysis Primer (M. Gribskov and J. Devereux, eds., M. Stockton Press 1991); and Carillo et al., 1988, *SIAM. J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al, 1990, *J. Mol. Biol.* 215:403-10). The BLASTX program is publicly available from the National Center for Biotechnology Information

TABLE II

Fc Fusion with Therapeutic Proteins

| Form of Fc | Fusion partner | Therapeutic implications | Reference |
| --- | --- | --- | --- |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, *J. Immunol.* 154: 5590-600 |
| IgG1 | TNF receptor | septic shock | Fisher et al., 1996, *N. Engl. J. Med.* 334: 1697-1702; Van Zee et al., 1996, *J. Immunol.* 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, *Nature* 337: 525-31 |
| IgG1, IgG3 | N-terminus of IL-2 | anti-cancer, antiviral | Harvill et al., 1995, *Immunotech.* 1: 95-105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, *J. Exp. Med.*, 174: 561-69 |

In one example, a human IgG hinge, CH2, and CH3 region may be fused at either the amino-terminus or carboxyl-terminus of the TSLPR polypeptides using methods known to the skilled artisan. In another example, a human IgG hinge, CH2, (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a TSLPR polypeptide can readily be obtained in a variety of ways including, without limitation, chemical synthesis, cDNA or genomic library screening, expression library screening, and/or PGR amplification of cDNA.

Recombinant DNA methods used herein are generally those set forth in Sambrook el al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a TSLPR polypeptide has been identified from one species, all or a portion of that gene may be used as a probe to identify orthologs or related genes from the same species. The probes or primers may be used to screen cDNA libraries from various tissue sources believed to express the TSLPR polypeptide. In addition, part or all of a nucleic acid molecule having the sequence as set forth in any of SEQ ID NO: 1, SEQ ID NO: 4, SEQ ID NO: 7, SEQ ID NO: 10, or SEQ ID NO: 11 may be used to screen a genomic library to identify and isolate a gene encoding the amino acid sequence of a TSLPR polypeptide. Typically, conditions of moderate or high stringency will be employed for screening to minimize the number of false positives obtained from the screening.

Nucleic acid molecules encoding the amino acid sequence of TSLPR polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a TSLPR polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a TSLPR polypeptide can be inserted into an expression vector. By introducing the expression vector into an appropriate host, the encoded TSLPR polypeptide may be produced in large amounts.

Another method for obtaining a suitable nucleic acid sequence is the polymerase chain reaction (PGR). In this method, cDNA is prepared from poly(A)+RNA or total RNA using the enzyme reverse transcriptase. Two primers, typically complementary to two separate regions of cDNA encoding the amino acid sequence of a TSLPR polypeptide, are then added to the cDNA along with a polymerase such as Taq polymerase, and the polymerase amplifies the cDNA region between the two primers.

Another means of preparing a nucleic acid molecule encoding the amino acid sequence of a TSLPR polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer supported synthesis using standard phosphoramidite chemistry. Typically, the DNA encoding the amino acid sequence of a TSLPR polypeptide will be several hundred nucleotides in length. Nucleic acids larger than about 100 nucleotides can be synthesized as several fragments using these methods. The fragments can then be ligated together to form the full-length nucleotide sequence of a TSLPR gene. Usually, the DNA fragment encoding the amino-terminus of the polypeptide will have an ATG, which encodes a methionine residue. This methionine may or may not be present on the mature form of the TSLPR polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a TSLPR polypeptide in a given host cell. Particular codon alterations will depend upon the TSLPR polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila_high.cod*," "Human_high.cod," "Maize_high.cod," and "Yeast_high.cod."

In some cases, it may be desirable to prepare nucleic acid molecules encoding TSLPR polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al, supra, for descriptions of mutagenesis techniques). Chemical synthesis using methods described by Engels et al, supra, may also be used to prepare such variants. Other methods known to the skilled artisan may be used as well.

Vectors and Host Cells

A nucleic acid molecule encoding the amino acid sequence of a TSLPR polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a TSLPR polypeptide may be amplified/expressed in prokaryotic, yeast, insect (baculovirus systems) and/or eukaryotic host cells. Selection of the host cell will depend in part on whether a TSLPR polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the TSLPR polypeptide coding sequence: the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the TSLPR polypeptide from the host cell. Affinity purification can be accomplished, for example, by column chromatography using antibodies against the tag as an affinity matrix. Optionally, the tag can subsequently be removed from the purified TSLPR polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate TSLPR polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the TSLPR gene flanking sequences—will have been previously identified by mapping and/or by restriction endonuclease digestion and can thus be isolated from the proper tissue source using the appropriate restriction endonucleases. In some cases, the full nucleotide sequence of a Hanking sequence may be known. Here, the flanking sequence may be synthesized using the methods described herein for nucleic acid synthesis or cloning.

Where all or only a portion of the flanking sequence is known, it may be obtained using PGR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a TSLPR polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a TSLPR polypeptide. As a result, increased quantities of TSLPR polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a TSLPR polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a TSLPR polypeptide out of the host cell. Typically, a nucleotide sequence encoding the signal sequence is positioned in the coding region of a TSLPR nucleic acid molecule, or directly at the 5' end of a TSLPR polypeptide coding region. Many signal sequences have been identified, and any of those that are functional in the selected host cell may be used in conjunction with a TSLPR nucleic acid molecule. Therefore, a signal sequence may be homologous (naturally occurring) or heterologous to the TSLPR nucleic acid molecule. Additionally, a signal sequence may be chemically synthesized using methods described herein. In most cases, the secretion of a TSLPR polypeptide from the host cell via the presence of a signal peptide will result in the removal of the signal peptide from the secreted TSLPR polypeptide. The signal sequence may be a component of the vector, or it may be a part of a TSLPR nucleic acid molecule that is inserted into the vector.

Included within the scope of this invention is the use of either a nucleotide sequence encoding a native TSLPR polypeptide signal sequence joined to a TSLPR polypeptide coding region or a nucleotide sequence encoding a heterologous signal sequence joined to a TSLPR polypeptide coding region. The heterologous signal sequence selected should be one that is recognized and processed, i.e., cleaved by a signal peptidase, by the host cell. For prokaryotic host cells that do not recognize and process the native TSLPR polypeptide signal sequence, the signal sequence is substituted by a prokaryotic signal sequence selected, for example, from the group of the alkaline phosphatase, penicillinase, or heat-stable enterotoxin II leaders. For yeast secretion, the native TSLPR polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired TSLPR polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the TSLPR gene especially where the gene used is a full-length genomic sequence or a fragment thereof. Where the nitron is not naturally occurring within the gene (as for most cDNAs), the intron may be obtained from another source. The position of the intron with respect to flanking sequences and the TSLPR gene is generally important, as the intron must be transcribed to be effective. Thus, when a TSLPR cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the TSLPR polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding TSLPR polypeptide by removing the promoter from the source DNA by restriction enzyme digestion and inserting the desired promoter sequence into the vector. The native TSLPR promoter sequence may be used to direct amplification and/or expression of a TSLPR nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling TSLPR gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.,* 75:3727-31); or the tac promoter (DeBoer et al., 1983, *Proc. Natl. Acad. Sci. U.S.A.,* 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.,* 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a TSLPR polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a TSLPR nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid; Stratagene Cloning Systems, La Jolla Calif.), PCR cloning plasmids designed for cloning Taq-amplified PCR products (e.g., TOPO™ TA Cloning® Kit and PCR2.1® plasmid derivatives; Invitrogen), and mammalian, yeast or virus vectors such as a baculovirus expression system (pBacPAK plasmid derivatives; Clontech).

After the vector has been constructed and a nucleic acid molecule encoding a TSLPR polypeptide has been inserted into the proper site of the vector, the completed vector may be inserted into a suitable host cell for amplification and/or polypeptide expression. The transformation of an expression vector for a TSLPR polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a TSLPR polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated TSLPR polypeptides. For example, one may use a transgenic milk-producing animal (a cow or goat, for example) and obtain the present glycosylated polypeptide in the animal milk. One may also use plants to produce TSLPR polypeptides, however, in general, the glycosylation occurring in plants is different from that produced in mammalian cells, and may result in a glycosylated product which is not suitable for human therapeutic use.

Polypeptide Production

Host cells comprising a TSLPR polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a TSLPR polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a TSLPR polypeptide has been designed to be secreted from the host cells, the majority of polypeptide may be found in the cell culture medium. If however, the TSLPR polypeptide is not secreted from the host cells, it will be present in the cytoplasm and/or the nucleus (for eukaryotic host cells) or in the cytosol (for gram-negative bacteria host cells).

For a TSLPR polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a TSLPR polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized TSLPR polypeptide can then be analyzed using gel electrophoresis, immunoprecipitation, or the like. If it is desired to isolate the TSLPR polypeptide, isolation may be accomplished using standard methods such as those described herein and in Marston et al., 1990, *Meth. Enz.*, 182:264-75.

In some cases, a TSLPR polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/ oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine. glutathione (GSH)/dithiobis GSH, cupric chloride, dithiothreitol(DTT)/dithiane DTT, and 2-2-mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a TSLPR polypeptide, then the polypeptide will be found primarily in the supernatant after centrifugation of the cell homogenate. The polypeptide may be further isolated from the supernatant using methods such as those described herein.

The purification of a TSLPR polypeptide from solution can be accomplished using a variety of techniques. If the polypeptide has been synthesized such that it contains a tag such as Hexahistidine (TSLPR polypeptide/hexaHis) or other small peptide such as FLAG (Eastman Kodak Co., New Haven, Conn.) or myc (Invitrogen) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of TSLPR polypeptide/polyHis. See, e.g., *Current Protocols in Molecular Biology* §10.11.8 (Ausubel et al., eds., Green Publishers Inc. and Wiley and Sons 1993).

Additionally, TSLPR polypeptides may be purified through the use of a monoclonal antibody that is capable of specifically recognizing and binding to a TSLPR polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

TSLPR polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized TSLPR polypeptides may be oxidized using methods set forth in these references to form disulfide bridges. Chemically synthesized TSLPR polypeptides are expected to have comparable biological activity to the corresponding TSLPR polypeptides produced recombinantly or purified from natural sources, and thus may be used interchangeably with a recombinant or natural TSLPR polypeptide.

Another means of obtaining TSLPR polypeptide is via purification from biological samples such as source tissues and or fluids in which the TSLPR polypeptide is naturally found. Such purification can be conducted using methods for protein purification as described herein. The presence of the TSLPR polypeptide during purification may be monitored, for example, using an antibody prepared against recombinantly produced TSLPR polypeptide or peptide fragments thereof.

A number of additional methods for producing nucleic acids and polypeptides are known in the art, and the methods can be used to produce polypeptides having specificity for TSLPR polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive TSLPR polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more TSLPR polypeptides. Suitable selective binding agents include, but are not limited to, antibodies and derivatives thereof, polypeptides, and small molecules. Suitable selective binding agents may be prepared using methods known in the art. An exemplary TSLPR polypeptide selective binding agent of the present invention is capable of binding a certain portion of the TSLPR polypeptide thereby inhibiting the binding of the polypeptide to a TSLPR polypeptide receptor.

Selective binding agents such as antibodies and antibody fragments that bind TSLPR polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the TSLPR polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a TSLPR polypeptide generally are produced in animals (e.g., rabbits or mice) by means of multiple subcutaneous or intraperitoneal injections of TSLPR polypeptide and an adjuvant. It may be useful to conjugate a TSLPR polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-TSLPR antibody titer.

Monoclonal antibodies directed toward TSLPR polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with TSLPR polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind TSLPR polypeptides. Using transgenic animals (e.g., mice) that are capable of producing a repertoire of human antibodies in the absence of endogenous immunoglobulin production such antibodies are produced by immunization with a TSLPR polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then crossbred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-TSLPR antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of TSLPR polypeptides. The antibodies will bind TSLPR polypeptides with an affinity that is appropriate for the assay method being employed.

For diagnostic applications, in certain embodiments, anti-TSLPR antibodies may be labeled with a detectable moiety. The detectable moiety can be any one that is capable of producing, either directly or indirectly, a detectable signal. For example, the detectable moiety may be a radioisotope, such as $^{3}H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a TSLPR polypeptide, or an immunologically reactive portion thereof) to compete with the test sample analyte (an TSLPR polypeptide) for binding with a limited amount of anti-TSLPR antibody. The amount of a TSLPR polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-TSLPR antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a TSLPR polypeptide. In one embodiment, antagonist antibodies of the invention are antibodies or binding fragments thereof which are capable of specifically binding to a TSLPR polypeptide and which are capable of inhibiting or eliminating the functional activity of a TSLPR polypeptide in vivo or in vitro. In preferred embodiments, the selective binding agent, e.g., an antagonist antibody, will inhibit the functional activity of a TSLPR polypeptide by at least about 50%, and preferably by at least about 80%. In another embodiment, the selective binding agent may be an anti-TSLPR polypeptide antibody that is capable of interacting with a TSLPR polypeptide binding partner (a ligand or receptor) thereby inhibiting or eliminating TSLPR polypeptide activity in vitro or in vivo. Selective binding agents, including agonist and antagonist anti-TSLPR polypeptide antibodies, are identified by screening assays that are well known in the art.

The invention also relates to a kit comprising TSLPR selective binding agents (such as antibodies) and other reagents useful for detecting TSLPR polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the TSLPR molecules of the invention, including, but not limited to: the identification and validation of TSLPR disease-related genes as targets for therapeutics; molecular toxicology of related TSLPR molecules and inhibitors thereof; stratification of populations and generation of surrogate markers for clinical trials; and enhancing related TSLPR polypeptide small molecule drag discovery by aiding in the identification of selective compounds in high throughput screens.

Chemical Derivatives

Chemically modified derivatives of TSLPR polypeptides may be prepared by one skilled in the art, given the disclosures described herein. TSLPR polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of any of SEQ ID NO: 2, SEQ ID NO: 5, or SEQ ID NO: 8, or other TSLPR polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached TSLPR polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of any of SEQ ID NO: 2, SEQ ID NO: 5, or SEQ ID NO: 8, or other TSLPR polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the TSLPR polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252, 714).

In another embodiment, TSLPR polypeptides may be chemically coupled to biotin. The biotin/TSLPR polypeptide molecules are then allowed to bind to avidin, resulting in tetravalent avidin/biotin/TSLPR polypeptide molecules. TSLPR polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present TSLPR polypeptide derivatives include those described herein for TSLPR polypeptides. However, the TSLPR polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native TSLPR polypeptide have been disrupted (i.e., "knocked out") such that the level of expression of TSLPR polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a TSLPR gene for that animal or a heterologous TSLPR gene is over-expressed by the animal, thereby creating a "transgenic" animal. Such transgenic animals may be prepared using well known methods such as those described in U.S. Pat. No 5,489,743 and PCT Pub. No. WO 94/28122.

The present invention further includes non-human animals in which the promoter for one or more of the TSLPR polypeptides of the present invention is either activated or inactivated (e.g., by using homologous recombination methods) to alter the level of expression of one or more of the native TSLPR polypeptides.

These non-human animals may be used for drug candidate screening. In such screening, the impact of a drug candidate on the animal may be measured, for example, drug candidates may decrease or increase the expression of the TSLPR gene. In certain embodiments, the amount of TSLPR polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of TSLPR Polypeptide Activity

In some situations, it may be desirable to identify molecules that are modulators, i.e., agonists or antagonists, of the activity of TSLPR polypeptide. Natural or synthetic molecules that modulate TSLPR polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a TSLPR polypeptide. Most commonly, a test molecule will interact directly with a TSLPR polypeptide. However, it is also contemplated that a test molecule may also modulate TSLPR polypeptide activity indirectly, such as by affecting TSLPR gene expression, or by binding to a TSLPR polypeptide binding partner (e.g., receptor or ligand). In one embodiment, a test molecule will bind to a TSLPR polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with TSLPR polypeptides are encompassed by the present invention. In certain embodiments, a TSLPR polypeptide is incubated with a test molecule under conditions that permit the interaction of the test molecule with a TSLPR polypeptide, and the extent of the interaction is measured. The test molecule can be screened in a substantially purified form or in a crude mixture.

In certain embodiments, a TSLPR polypeptide agonist or antagonist may be a protein, peptide, carbohydrate, lipid, or small molecular weight molecule that interacts with TSLPR polypeptide to regulate its activity. Molecules which regulate TSLPR polypeptide expression include nucleic acids which are complementary to nucleic acids encoding a TSLPR polypeptide, or are complementary to nucleic acids sequences which direct or control the expression of TSLPR polypeptide, and which act as anti-sense regulators of expression.

Once a test molecule has been identified as interacting with a TSLPR polypeptide, the molecule may be further evaluated for its ability to increase or decrease TSLPR polypeptide activity. The measurement of the interaction of a test molecule with TSLPR polypeptide may be carried out in several formats, including cell-based binding assays, membrane binding assays, solution-phase assays, and immunoassays. In general, a test molecule is incubated with a TSLPR polypeptide for a specified period of time, and TSLPR polypeptide activity is determined by one or more assays for measuring biological activity.

The interaction of test molecules with TSLPR polypeptides may also be assayed directly using polyclonal or monoclonal antibodies in an immunoassay. Alternatively, modified forms of TSLPR polypeptides containing epitope tags as described herein may be used in solution and immunoassays.

In the event that TSLPR polypeptides display biological activity through an interaction with a binding partner (e.g., a receptor or a ligand), a variety of in vitro assays may be used to measure the binding of a TSLPR polypeptide to the corresponding binding partner (such as a selective binding agent, receptor, or ligand). These assays may be used to screen test molecules for their ability to increase or decrease the rate and/or the extent of binding of a TSLPR polypeptide to its binding partner. In one assay, a TSLPR polypeptide is immobilized in the wells of a microtiter plate. Radiolabeled TSLPR polypeptide binding partner (for example, iodinated TSLPR polypeptide binding partner) and a test molecule can then be added either one at a time (in either order) or simultaneously to the wells. After incubation, the wells can be washed and counted for radioactivity, using a scintillation counter, to determine the extent to which the binding partner bound to the TSLPR polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing TSLPR polypeptide binding partner to the microtiter plate wells, incubating with the test molecule and radiolabeled TSLPR polypeptide, and determining the extent of TSLPR polypeptide binding. See, e.g., *Current Protocols in Molecular Biology*, chap. 18 (Ausubel et al., eds., Green Publishers Inc. and Wiley and Sons 1995).

As an alternative to radiolabeling, a TSLPR polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a TSLPR polypeptide or to a TSLPR polypeptide binding partner, and which is conjugated to biotin, may also be used for purposes of detection following incubation of the complex with enzyme-linked streptavidin linked to AP or HRP.

A TSLPR polypeptide or a TSLPR polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a TSLPR polypeptide and its binding partner can be assessed using the methods described herein. Alternatively, the substrate-protein complex can be immobilized in a column with the test molecule and complementary protein passing through the column. The formation of a complex between a TSLPR polypeptide and its binding partner can then be assessed using any of the techniques described herein (e.g., radiolabelling or antibody binding).

Another in vitro assay that is useful for identifying a test molecule that increases or decreases the formation of a complex between a TSLPR polypeptide binding protein and a TSLPR polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either TSLPR polypeptide or a TSLPR polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a TSLPR polypeptide and a TSLPR polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a TSLPR polypeptide and TSLPR polypeptide binding partner. The assays may be automated to screen compounds generated in phage display, synthetic peptide, and chemical synthesis libraries.

Compounds which increase or decrease the formation of a complex between a TSLPR polypeptide and a TSLPR polypeptide binding partner may also be screened in cell culture using cells and cell lines expressing either TSLPR polypeptide or TSLPR polypeptide binding partner. Cells and cell lines may be obtained from any mammal, but preferably will be from human or other primate, canine, or rodent sources. The binding of a TSLPR polypeptide to cells expressing TSLPR polypeptide binding partner at the surface is evaluated in the presence or absence of test molecules, and the extent of binding may be determined by, for example, flow cytometry using a biotinylated antibody to a TSLPR polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the TSLPR gene. In certain embodiments, the amount of TSLPR polypeptide or a TSLPR polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 13) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-

R-K-K-R-R-Q-R-R-R; SEQ ID NO: 14), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a TSLPR antagonist (such as an anti-TSLPR selective binding agent, small molecule, soluble receptor, or antisense oligonucleotide) can be administered intracellularly to inhibit the activity of a TSLPR molecule. As used herein, the term "TSLPR molecule" refers to both TSLPR nucleic acid molecules and TSLPR polypeptides as defined herein. Where desired, the TSLPR protein itself may also be internally administered to a cell using these procedures. See also, Straus, 1999, *Science* 285:1466-67.

Cell Source Identification Using TSLPR Polypeptide

In accordance with certain embodiments of the invention, it may be useful to be able to determine the source of a certain cell type associated with a TSLPR polypeptide. For example, it may be useful to determine the origin of a disease or pathological condition as an aid in selecting an appropriate therapy. In certain embodiments, nucleic acids encoding a TSLPR polypeptide can be used as a probe to identify cells described herein by screening the nucleic acids of the cells with such a probe. In other embodiments, one may use anti-TSLPR polypeptide antibodies to test for the presence of TSLPR polypeptide in cells, and thus, determine if such cells are of the types described herein.

TSLPR Polypeptide Compositions and Administration

Therapeutic compositions are within the scope of the present invention. Such TSLPR polypeptide pharmaceutical compositions may comprise a therapeutically effective amount of a TSLPR polypeptide or a TSLPR nucleic acid molecule in admixture with a pharmaceutically or physiologically acceptable formulation agent selected for suitability with the mode of administration. Pharmaceutical compositions may comprise a therapeutically effective amount of one or more TSLPR polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990).

The optimal pharmaceutical composition will be determined by a skilled artisan depending upon, for example, the intended route of administration, delivery format, and desired dosage. See, e.g., Remington's Pharmaceutical Sciences, supra. Such compositions may influence the physical state, stability, rate of in vivo release, and rate of in vivo clearance of the TSLPR molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, TSLPR polypeptide compositions may be prepared for storage by mixing the selected composition having the desired degree of purity with optional formulation agents (Remington's Pharmaceutical Sciences, supra) in the form of a lyophilized cake or an aqueous solution. Further, the TSLPR polypeptide product may be formulated as a lyophilizate using appropriate excipients such as sucrose.

The TSLPR polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired TSLPR molecule in a pharmaceutically acceptable vehicle. A particularly suitable vehicle for parenteral injection is sterile distilled water in which a TSLPR molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, TSLPR polypeptide may be formulated as a dry powder for inhalation. TSLPR polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, TSLPR polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the TSLPR polypeptide. Diluents, flavorings, low melting point waxes, vegetable oils, lubricants, suspending agents, tablet disintegrating agents, and binders may also be employed.

Another pharmaceutical composition may involve an effective quantity of TSLPR polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional TSLPR polypeptide pharmaceutical compositions will be evident to those skilled in the art, including formulations involving TSLPR polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The TSLPR pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a TSLPR pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the TSLPR molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the TSLPR molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use TSLPR polypeptide pharmaceutical compositions in an ex vivo manner. In such instances, cells, tissues, or organs that have been removed from the patient are exposed to TSLPR polypeptide pharmaceutical compositions after which the cells, tissues, or organs are subsequently implanted back into the patient.

In other cases, a TSLPR polypeptide can be delivered by implanting certain cells that have been genetically engineered, using methods such as those described herein, to express and secrete the TSLPR polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more TSLPR polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent TSLPR gene, or an under-expressed gene, and thereby produce a cell which expresses therapeutically efficacious amounts of TSLPR polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28: Thomas and Capecchi, 1987, *Cell* 51:503-12: Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a TSLPR polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired TSLPR polypeptide. The control element controls a portion of the DNA present in the host cell genome. Thus, the expression of the desired TSLPR polypeptide may be achieved not by transfection of DNA that encodes the TSLPR gene itself, but rather by the use of targeting DNA (containing regions of homology with the endogenous gene of interest) coupled with DNA regulatory segments that provide the endogenous gene sequence with recognizable signals for transcription of a TSLPR gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, TSLPR polypeptide production from a cell's endogenous TSLPR gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic TSLPR polypeptide coding region. A plasmid containing a recombination site homologous to the site that was placed just upstream of the genomic TSLPR polypeptide coding region is introduced into the modified cell line along with the appropriate recombinase enzyme. This recombinase causes the plasmid to integrate, via the plasmid's recombination site, into the recombination site located just upstream of the genomic TSLPR polypeptide coding region in the cell line (Baubonis and Sauer, 1993, *Nucleic Acids Res*, 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de nova or increased TSLPR polypeptide production from the cell's endogenous TSLPR gene.

A further method to use the cell line in which the site specific recombination sequence had been placed just upstream of the cell's endogenous genomic TSLPR polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.,* 5:521-27; Sauer, 1993, *Methods Enzymol.,* 225:890-900) that would create a new or modified transcriptional unit resulting in de novo or increased TSLPR polypeptide production from the cell's endogenous TSLPR gene.

An additional approach for increasing, or causing, the expression of TSLPR polypeptide from a cell's endogenous TSLPR gene involves increasing, or causing, the expression of a gene or genes (e.g., transcription factors) and/or decreasing the expression of a gene or genes (e.g., transcriptional repressors) in a manner which results in de novo or increased TSLPR polypeptide production from the cell's endogenous TSLPR gene. This method includes the introduction of a non-naturally occurring polypeptide (e.g., a polypeptide comprising a site specific DNA binding domain fused to a transcriptional factor domain) into the cell such that de novo or increased TSLPR polypeptide production from the cell's endogenous TSLPR gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice donor site is 3' of the exon.

If the sequence of a particular gene is known, such as the nucleic acid sequence of TSLPR polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a TSLPR polypeptide, which nucleotides may be used as targeting sequences.

TSLPR polypeptide cell therapy, e.g., the implantation of cells producing TSLPR polypeptides, is also contemplated. This embodiment involves implanting cells capable of synthesizing and secreting a biologically active form of TSLPR polypeptide. Such TSLPR polypeptide-producing cells can be cells that are natural producers of TSLPR polypeptides or may be recombinant cells whose ability to produce TSLPR polypeptides has been augmented by transformation with a gene encoding the desired TSLPR polypeptide or with a gene augmenting the expression of TSLPR polypeptide. Such a modification may be accomplished by means of a vector suitable for delivering the gene as well as promoting its expression and secretion. In order to minimize a potential immunological reaction in patients being administered a TSLPR polypeptide, as may occur with the administration of a polypeptide of a foreign species, it is preferred that the natural cells producing TSLPR polypeptide be of human origin and produce human TSLPR polypeptide. Likewise, it is preferred that the recombinant cells producing TSLPR polypeptide be transformed with an expression vector containing a gene encoding a human TSLPR polypeptide.

Implanted cells may be encapsulated to avoid the infiltration of surrounding tissue. Human or non-human animal cells may be implanted in patients in biocompatible, semipermeable polymeric enclosures or membranes that allow the release of TSLPR polypeptide, but that prevent the destruction of the cells by the patient's immune system or by other detrimental factors from the surrounding tissue. Alternatively, the patient's own cells, transformed to produce TSLPR polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operativeiy linked to promoters that are not subject to downregulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of TSLPR polypeptides is also envisioned. One example of a gene therapy technique is to use the TSLPR gene (either genomic DNA, cDNA, and/or synthetic DNA) encoding a TSLPR polypeptide which may be operably linked to a constitutive or inducible promoter to form a "gene therapy DNA construct." The promoter may be homologous or heterologous to the endogenous TSLPR gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the TSLPR gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding TSLPR polypeptide into cells via local injection of a TSLPR nucleic acid molecule or by other appropriate viral or non-viral delivery vectors. Hefti 1994, *Neurobiology* 25:1418-35. For example, a nucleic acid molecule encoding a TSLPR polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a TSLPR polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that TSLPR gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous TSLPR polypeptide expression in a cell via gene therapy is to insert one or more enhancer elements into the TSLPR polypeptide promoter, where the enhancer elements can serve to increase transcriptional activity of the TSLPR gene. The enhancer elements used will be selected based on the tissue in which one desires to activate the gene—enhancer elements known to confer promoter activation in that tissue will be selected. For example, if a gene encoding a TSLPR polypeptide is to be "turned on" in T-cells, the lck promoter enhancer element may be used. Here, the functional portion of the transcriptional element to be added may be inserted into a fragment of DNA containing the TSLPR polypeptide promoter land optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease TSLPR polypeptide expression by modifying the nucleotide sequence of the endogenous promoter. Such modification is typically accomplished via homologous recombination methods. For example, a DNA molecule containing all or a portion of the promoter of the TSLPR gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding TSLPR gene. The deletion of the TATA box or the transcription activator binding site in the promoter may be accomplished by generating a DNA construct comprising all or the relevant portion of the TSLPR polypeptide promoter (from the same or a related species as the TSLPR gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex: vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

TSLPR nucleic acid molecules, polypeptides, and agonists and antagonists thereof can be used to treat, diagnose, ameliorate, or prevent a number of diseases, disorders, or conditions, including TSLP-related diseases, disorders, or conditions. TSLP-related diseases, disorders, or conditions may be related to B-cell development, T-cell development, T-cell receptor gene rearrangement, or regulation of the Stat5 transcription factor. Diseases caused by or mediated by undesirable levels of TSLP are encompassed within the scope of the invention. Undesirable levels include excessive levels of TSLP and subnormal levels of TSLP.

TSLPR polypeptide agonists and antagonists include those molecules that regulate TSLPR polypeptide activity and either increase or decrease at least one activity of the mature form of the TSLPR polypeptide. Agonists or antagonists may be co-factors, such as a protein, peptide, carbohydrate, lipid, or small molecular weight molecule, which interact with TSLPR polypeptide and thereby regulate its activity. Potential polypeptide agonists or antagonists include antibodies that react with either soluble or membrane-bound forms of TSLPR polypeptides that comprise part or all of the extracellular domains of the said proteins. Molecules that regulate TSLPR polypeptide expression typically include nucleic acids encoding TSLPR polypeptide that can act as anti-sense regulators of expression.

TSLPR nucleic acid molecules, polypeptides, and agonists and antagonists thereof may be used (simultaneously or sequentially) in combination with one or more cytokines, growth factors, antibiotics, anti-inflammatories, and/or chemotherapeutic agents as is appropriate for the condition being treated.

Other diseases or disorders caused by or mediated by undesirable levels of TSLPR polypeptides are encompassed within the scope of the invention. Undesirable levels include excessive levels of TSLPR polypeptides and sub-normal levels of TSLPR polypeptides.

Uses of TSLPR Nucleic Acids and Polypeptides

Nucleic acid molecules of the invention (including those that do not themselves encode biologically active polypeptides) may be used to map the locations of the TSLPR gene and related genes on chromosomes. Mapping may be done by techniques known in the art, such as PCR amplification and in situ hybridization.

TSLPR nucleic acid molecules (including those that do not themselves encode biologically active polypeptides) may be useful as hybridization probes in diagnostic assays to test, either qualitatively or quantitatively, for the presence of a TSLPR nucleic acid molecule in mammalian tissue or bodily fluid samples.

Other methods may also be employed where it is desirable to inhibit the activity of one or more TSLPR polypeptides. Such inhibition may be effected by nucleic acid molecules that are complementary to and hybridize to expression control sequences (triple helix formation) or to TSLPR mRNA. For example, antisense DNA or RNA molecules, which have a sequence that is complementary to at least a portion of a TSLPR gene can be introduced into the cell. Anti-sense probes may be designed by available techniques using the sequence of the TSLPR gene disclosed herein. Typically, each such antisense molecule will be complementary to the start site (5' end) of each selected TSLPR gene. When the antisense molecule then hybridizes to the corresponding TSLPR mRNA, translation of this mRNA is prevented or reduced. Anti-sense inhibitors provide information relating to the decrease or absence of a TSLPR polypeptide in a cell or organism.

Alternatively, gene therapy may be employed to create a dominant-negative inhibitor of one or more TSLPR polypeptides. In this situation, the DNA encoding a mutant polypeptide of each selected TSLPR polypeptide can be prepared and introduced into the cells of a patient using either viral or non-viral methods as described herein. Each such mutant is typically designed to compete with endogenous polypeptide in its biological role.

In addition, a TSLPR polypeptide, whether biologically active or not, may be used as an immunogen, that is, the polypeptide contains at least one epitope to which antibodies may be raised. Selective binding agents that bind to a TSLPR polypeptide (as described herein) may be used for in vivo and in vitro diagnostic purposes, including, but not limited to, use in labeled form to detect the presence of TSLPR polypeptide in a body fluid or cell sample. The antibodies may also be used to prevent, treat, or diagnose a number of diseases and disorders, including those recited herein. The antibodies may bind to a TSLPR polypeptide so as to diminish or block at least one activity characteristic of a TSLPR polypeptide, or may bind to a polypeptide to increase at least one activity characteristic of a TSLPR polypeptide (including by increasing the pharmacokinetics of the TSLPR polypeptide).

The murine and human TSLPR nucleic acids of the present invention are also useful tools for isolating the corresponding chromosomal TSLPR polypeptide genes. For example, mouse chromosomal DNA containing TSLPR sequences can be used to construct knockout mice, thereby permitting an examination of the in vivo role for TSLPR polypeptide. The human TSLPR genomic DNA can be used to identify heritable tissue-degenerating diseases.

The following examples are intended for illustration purposes only, and should not be construed as limiting the scope of the invention in any way.

EXAMPLE 1

Cloning of the Murine and Human TSLPR Polypeptide Genes

Generally, materials and methods as described in Sambrook et al., supra were used to clone and analyze the genes encoding murine and human TSLPR polypeptides.

Sequences encoding the murine TSLPR polypeptide were identified in a BLAST search of an EST database using sequences corresponding to the cytoplasmic domain of the erythropoietin receptor. Several overlapping murine ESTs, which encode a novel type I cytokine receptor molecule, were obtained in the BLAST search. The cytoplasmic domain of the cytokine receptor encoded by these sequences was found to share significant similarity to that of the common cytokine receptor γ chain ($\gamma_c$), the erythropoietin receptor, and the IL-9 receptor α chain.

The common cytokine receptor γ chain is an essential subunit of the receptors for IL-2, IL-4, IL-7, IL-9, and IL-15 (Noguchi et al., 1993, Science 262:1877-80; Kondo et al., 1994, Science 263:1453-54; Kendo et al., 1993, Science 262: 1874-77; Russell et al., 1994, Science 266:1042-45; Takeshita et al., 1992, Science 257:379-82; Russell et al., 1993, Science 262:1880-83; Giri et al., 1994, EMBO J. 13:2822-30; Kunura et al., 1995, Int. Immunol. 7:115-20). The mutation of $\gamma_c$ in humans can result in X-linked severe combined immunodeficiency (Noguchi et al., 1993, Cell 73:147-57; Leonard et al., 1995, Immunol. Rev. 148:97-114).

Since none of the ESTs sequences identified in the BLAST search contained the entire open reading frame for TSLPR polypeptide, a mouse embryo library was screened to obtain a full-length cDNA. The positive colony containing the longest insert was used to prepare plasmid DNA by standard methods. The cDNA insert from this colony was 2 kb in length. DNA sequence analysis confirmed that the clone contained the entire reading frame for TSLPR polypeptide.

Sequence analysis of the full-length cDNA for murine TSLPR polypeptide indicated that the gene comprises a 1110 bp open reading frame encoding a protein of 370 amino acids and possessing a potential signal peptide of 17 amino acids in length at its amino-terminus (FIGS. 1A-1B; predicted signal peptide indicated by underline). The open reading frame was found to encode a type I transmembrane protein having two potential N-linked glycosylation sites and a cytoplasmic domain of 104 amino acids containing a single tyrosine residue.

Figure 2:
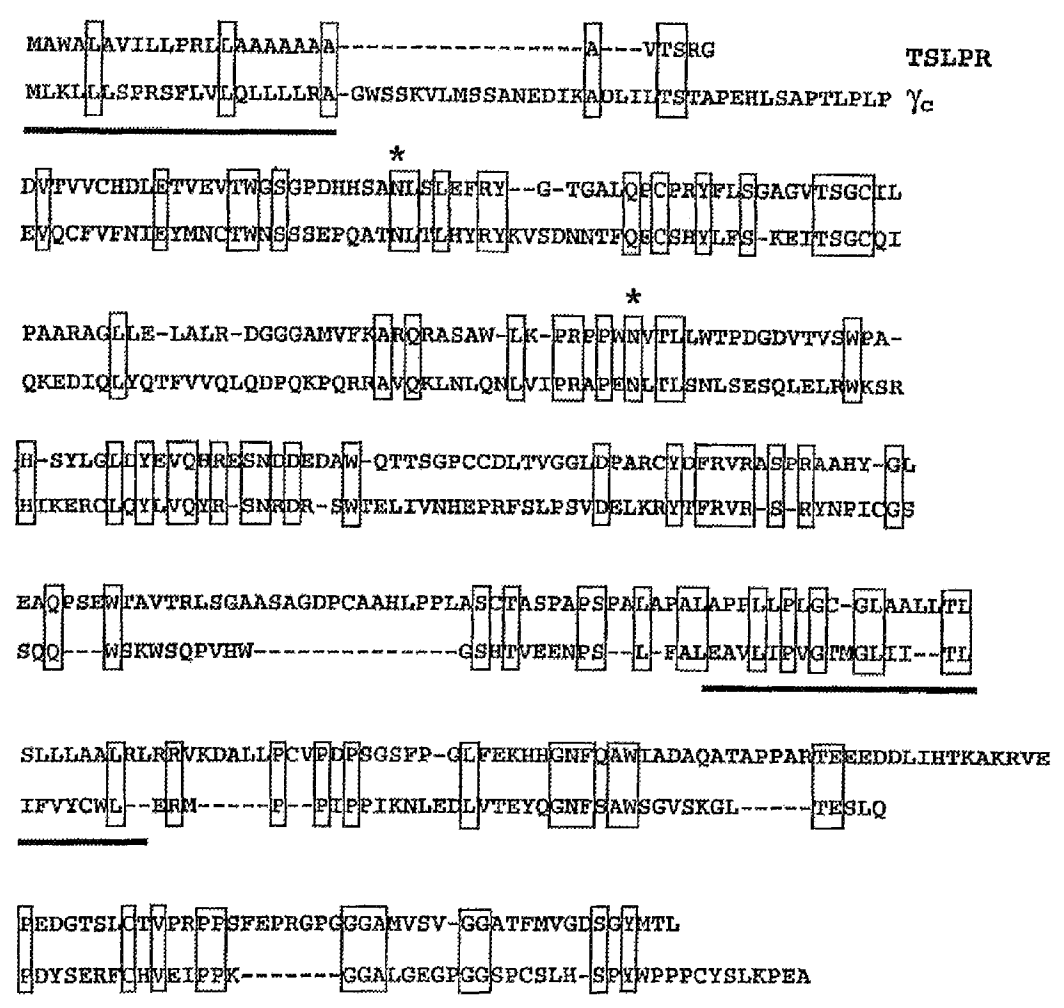

In contrast, murine $\gamma_c$ comprises 369 amino acids a has a cytoplasmic domain of 86 amino acids containing two tyrosine residues (Kumaki et al., 1993, Biochem. Biophys. Res. Commun. 193:356-63; Cao et al., 1993, Proc. Natl. Acad. Sci. U.S.A. 90:8464-68; Kobayash et al., 1993, Gene 130:303-04). FIG. 2 illustrates an amino acid sequence alignment of murine TSLPR polypeptide (upper sequence) and murine $\gamma_c$ (lower sequence). Murine TSLPR polypeptide was found to share 26% sequence identity and 47% sequence similarity with $\gamma_c$ at the amino acid level. The sequence of murine TSLPR polypeptide is somewhat atypical for type I cytokine receptors in that only one pair of cysteines is conserved and the W-S-X-W-S (SEQ ID NO: 15) motif is replaced by a W-T-A-V-T (SEQ ID NO: 16) motif. The predicted molecular weight of murine TSLPR polypeptide is 37 kD.

Sequences encoding the human TSLPR polypeptide were identified in a BLAST search of a proprietary database of cDNA sequences (Amgen, Thousand Oaks, Calif.) using the murine TSLPR nucleic acid sequence as a query sequence. Two clones containing human cDNA sequences and sharing the greatest homology with the murine TSLPR nucleic acid sequence were identified in this search: 9604927 (SEQ ID NO: 10) and 9508990 (SEQ ID NO: 11). Sequence analysis of the full-length cDNA for human TSLPR polypeptide (as contained in Clone 9604927) indicated that the human TSLPR gene comprises an open reading frame of 1113 bp encoding a protein of 371 amino acids and possessing a potential signal peptide of 22 amino acids in length at its amino-terminus (FIGS. 3A-3B; predicted signal peptide indicated by underline).

Clone 9508990 contains an open reading frame of 1137 bp encoding a protein of 379 amino acids (FIGS. 4A-4B). This clone essentially comprises the full-length human TSLPR polypeptide sequence and an additional 8 amino acids at the carboxyl-terminus corresponding to the FLAG epitope. FIG. 5 illustrates an amino acid sequence alignment of murine TSLPR polypeptide (upper sequence) and human TSLPR polypeptide (lower sequence). The availability of murine and human TSLPR nucleic acid and amino acid sequences will further aid in the elucidation of signal transduction pathways utilized by TSLP.

EXAMPLE 2

TSLPR Polypeptide Expression

A cDNA construct encoding the entire open reading frame for murine TSLPR was transcribed and translated in vitro in the presence of $^{35}$S-methionine and the product resolved by SDS-PAGE. FIG. 6A illustrates an autoradiogram of the gel in which a single species of approximately 40 kD was obtained.

Figure 6B:
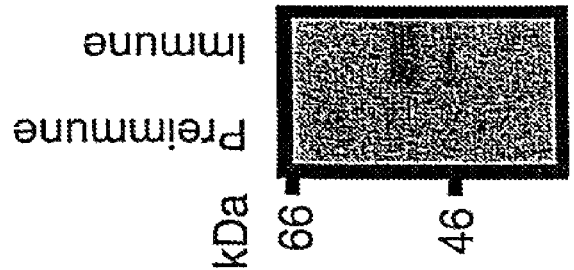
Figure 6A:

FIG. 6B illustrates the immunoprecipitation of murine TSLPR polypeptide in the growth factor-dependent pre-B-cell line NAG8/7 using a rabbit polyclonal antiserum raised against the extracellular domain of murine TSLPR polypeptide. The rabbit polyclonal antiserum was generated against murine TSLPR polypeptide-glutathione S-transferase fusion protein which was cloned into the pGEX4T2 expression vector (Pharmacia) and expressed in bacteria. Prior to metabolic labeling, NAG8/7 cells were grown in RPMI supplemented with 10% fetal bovine serum, antibiotics, and TSLP.

NAG8/7 cells were metabolically labeled with $^{35}$S-methionine and cysteine, lysed in 50 mM Tris, pH 7.4, 150 mM NaCl, 1% Triton X-100, and protease inhibitors, and the lysates incubated overnight with either rabbit polyclonal antiserum (lane 2) or pre-immune serum (lane 1). The immune complexes were captured with Protein G sepharosel, washed in lysis buffer, and then resolved by SDS-PAGE. The polyclonal antiserum specifically immunoprecipitated a broad band of approximately 50 kD in a pre-B-cell line NAG8/7 (FIG. 6B). The larger size of the immunoprecipitated product as compared with the product generated by in vitro translation is consistent with the addition of N-linked carbohydrate moieties in the extracellular domain. Flow cytometric analysis of transfected 293 cells and several hematopoietic cell lines (i.e., 32D, BaF3, and WEHI-3) confirmed that murine TSLPR was expressed at the cell surface.

EXAMPLE 3

TSLPR mRNA Expression

The tissue distribution of murine TSLPR was examined by northern blot analysis. A mouse multiple tissue northern blot (Clontech, Palo Alto, Calif.) was screened with a $^{32}$P-labeled TSLPR cDNA probe using standard techniques. Murine TSLPR mRNA transcripts were detected in nearly all of the tissues examined, with highest levels of expression being detected in the lung, liver, and testis (FIG. 6C). Lower levels of expression were detected in the heart, brain, spleen, and skeletal muscle. Two transcripts of approximately 2 kb and 2.2 kb were detected in some tissues, whereas only a single transcript of approximately 2 kb was detected in other tissues. The broad tissue distribution of murine TSLPR mRNA differs from the relatively restricted lympho-hematopoietic pattern of expression observed for $\gamma_c$.

The expression of TSLPR mRNA can be localized by in situ hybridization as follows. A panel of normal embryonic and adult mouse tissues is fixed in 4% paraformaldehyde, embedded in paraffin, and sectioned at 5 µm. Sectioned tissues are permeabilized in 0.2 M HCl, digested with Proteinase K, and acetylated with triethanolamine and acetic anhydride. Sections are prehybridized for 1 hour at 60° C. in hybridization solution (300 mM NaCl, 20 mM Tris-HCl, pH 8.0, 5 mM EDTA. 1× Denhardt's solution, 0.2% SDS, 10 mM DTT, 0.25 mg/ml tRNA, 25 µg/ml polyA, 25 µg/ml polyC and 50% formamide) and then hybridized overnight at 60° C. in the same solution containing 10% dextran and $2\times10^4$ cpm/µl of a $^{33}$P-labeled antisense riboprobe complementary to the human TSLPR gene. The riboprobe is obtained by in vitro transcription of a clone containing human TSLPR cDNA sequences using standard techniques.

Following hybridization, sections are rinsed in hybridization solution, treated with RNaseA to digest unhybridized probe, and then washed in 0.1×SSC at 55° C. for 30 minutes. Sections are then immersed in NTB-2 emulsion (Kodak, Rochester, N.Y.), exposed for 3 weeks at 4° C., developed, and counterstained with hematoxylin and eosin. Tissue morphology and hybridization signal are simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymis, prostate, seminal vesicle, and vas deferens in the male), BAT and WAT (subcutaneous, peri-renal), bone (femur), skin, breast, and skeletal muscle.

EXAMPLE 4

Biological Activity of Murine TSLPR Polypeptide

The similarity between murine TSLPR polypeptide and the erythropoietin receptor suggested that murine TSLPR, like the erythropoietin receptor, could be activated by homodimerization. This was examined in a proliferation assay using a chimeric construct derived from the extracellular and transmembrane domains of the c-Kit receptor and the cytoplasmic domain of murine TSLPR polypeptide. To generate this construct, the extracellular and transmembrane domains of c-Kit and the cytoplasmic domain of TSLPR were amplified by PCR and ligated into the retroviral vector pMX-IRES-GFP using standard techniques.

IL-2-dependent CTLL2 cells were stably transfected with expression constructs encoding c-Kit/TSLPR and c-Kit/β, c-Kit/β and c-Kit/γ, or c-Kit/γ alone. The constructs for c-Kit/β and c-Kit/γ were as described by Nelson et al., 1994, *Nature* 369:333-36. Following transfection, CTLL2 cells were deprived of IL-2, transferred into 48-well dishes at 10,000 cells/well, and grown in the absence or presence of Stem Cell Factor (SCF), the ligand for c-Kit. Cells were counted after 7 days of growth in culture.

Figure 7:
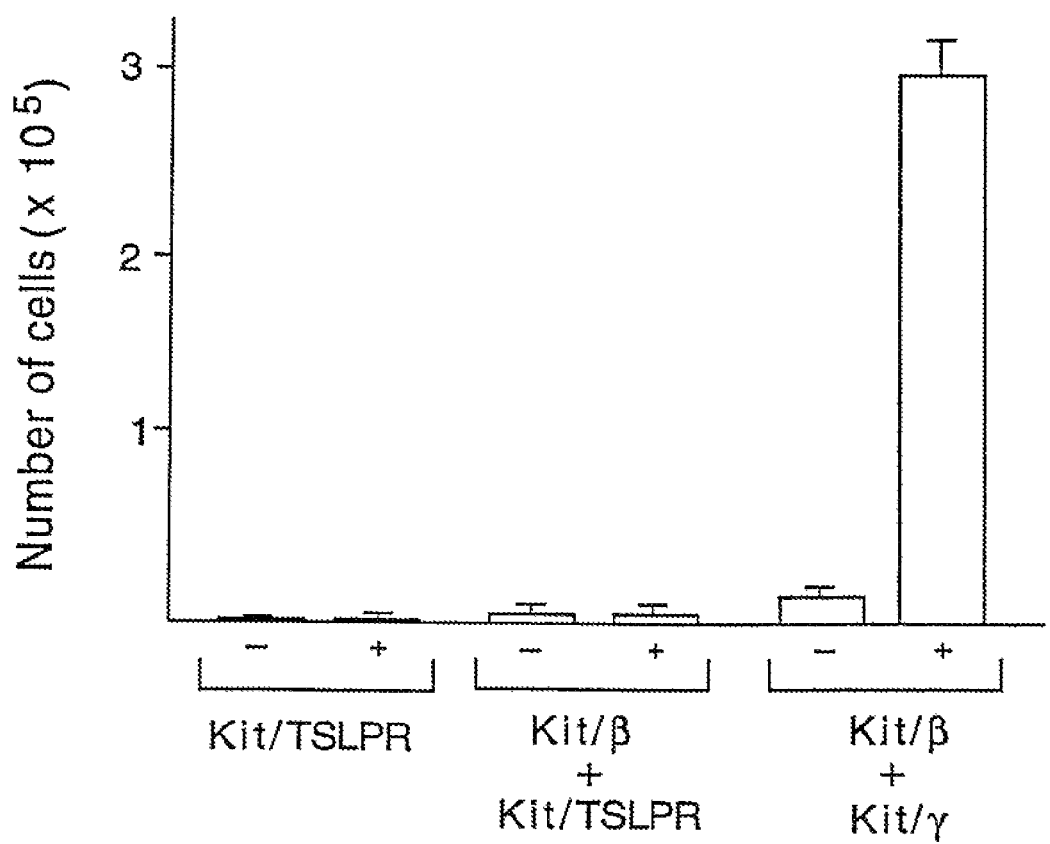
FIG. 7 illustrates the results obtained in proliferation assays using cells transfected with chimeric expression constructs for c-Kit/$\gamma_c$, c-Kit/TSLPR and c-Kit/β, or c-Kit/$\gamma_c$ and c-Kit/β.

FIG. 7 illustrates that when IL-2 was replaced by SCF, CTLL2 cells stably expressing chimeric c Kit/TSLPR polypeptide were unable to grow, suggesting that simple homodimerization of the cytoplasmic domain of murine TSLPR polypeptide is insufficient to induce a proliferative signal. Similar results have been obtained in proliferation experiments using a chimeric c-Kit/$\gamma_c$ polypeptide (Nelson et al., supra). Furthermore, when CTLL2 cells were co-transfected with c-Kit/TSLPR and c-Kit/β, the cells were still unable to proliferate. However, CTLL2 cells co-transfected with c-Kit/β and c-Kit/γ were able to proliferate following incubation with SCF. This suggested that the cytoplasmic domain of the IL-2Rβ chain could not cooperate with the cytoplasmic domain of murine TSLPR polypeptide to initiate proliferation, and that murine TSLPR polypeptide might oligomerize with some other receptor to participate in signal transduction.

The similarity between murine TSLPR polypeptide and $\gamma_c$ suggested that murine TSLPR may have the capacity to bind to some of the members of the IL-2 cytokine subfamily. This was examined in an affinity labeling assay using $^{125}$I-labeled IL-2, IL-4, IL-7, and IL-15. Prior to the addition of an $^{125}$I-labeled cytokine, 293 cells were reconstituted with the cytokine specific subunits IL-2Rβ, IL-4Rα, or IL-7Rα in the presence of either $\gamma_c$ or murine TSLPR polypeptide. None of the ligands examined exhibited binding when murine TSLPR was co-expressed with a cytokine specific subunit, even though the ligands efficiently bound when $\gamma_c$ was co-expressed with a cytokine specific subunit. This suggested that murine TSLPR polypeptide either bound a novel cytokine or bound a known cytokine in conjunction with a novel or untested subunit.

Thymic stromal lymphopoictm (TSLP) is a cytokine whose biological activities overlap with those of IL-7. TSLP activity was originally identified in the conditioned medium of a thymic stromal cell line that supported the development of murine IgM$^+$ B-cells from fetal liver hematopoietic progenitor cells (Friend et al., 1994 *Exp. Hematol.* 22:321-28). Moreover, TSLP can promote B-cell lymphopoiesis in long-term bone marrow cultures and can co-stimulate both thymocytes and mature T cells (Friend et al., supra; Levin et al., 1999. *J. Immunol.* 162:677-83).

Although IL-7 also possesses these activities (Suda et al., 1989. *Blood* 74:1936-41; Lee et al., 1989, *J. Immunol.* 142: 3875-83; Sudo et al., 1989, *J. Exp. Med.* 170:333-38). TSLP is unique in that it promotes B lymphopoiesis to the IgM$^+$ immature B-cell stage, while IL-7 primarily facilitates production of IgM$^-$ pre-B-cells (Levin et al., supra; Candeias et al., 1997, *Immunity* 6:501-08). One possible explanation for the overlapping biological activities of IL-7 and TSLP is that TSLP signals via a receptor containing the IL-7Rα chain (Levin et al., supra). However, antibody inhibition experiments have indicated that TSLP does not require $\gamma_c$ to exert its effects (Levin et al., supra). These results suggested that TSLP would bind murine TSLPR polypeptide in the presence of IL-7Rα.

The binding of TSLP to TSLPR polypeptide in the presence of IL-7Rα was examined in affinity labeling assays. Affinity labeling assays were performed by adding 1-5 nM of $^{125}$I-labeled TSLP to 5×10$^6$ 293 cells transfected with expression constructs for murine IL-7Rα, murine TSLPR polypeptide, murine IL-7Rα and murine TSLPR polypeptide, or human IL-7Rα and murine TSLPR polypeptide, Iodinated TSLP was prepared by adding IODO-GEN (Pierce, Rockford, Ill.) and 2 mCi $^{125}$I to 1 μg of TSLP. A specific activity of approximately 200-300 μCi/μg was obtained by this method. Prior to affinity labeling, 293 cells were transiently transfected using the calcium phosphate method (Eppendorf-5 Prime, Boulder, Colo.). Following a 2 hour incubation with $^{125}$I-TSLP, cells were cross-linked with 0.1 mg/ml disuccinimidyl suberate (Pierce), lysed in lysis buffer, and the lysates resolved by SDS-PAGE.

Figures 8A, 8B, 8C:
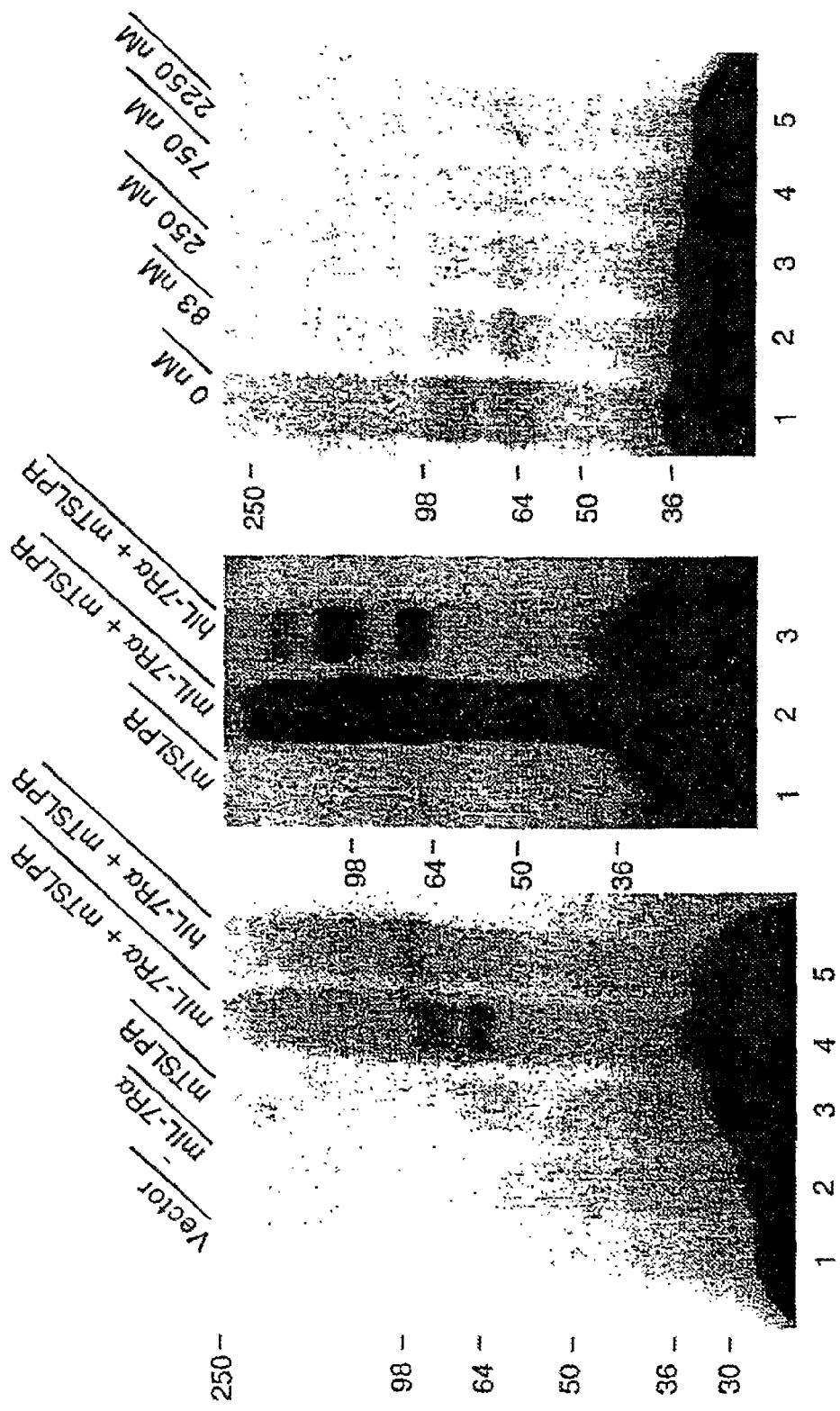
FIGS. 8A-8C illustrate the results obtained in affinity labeling assays in which $^{125}$I-TSLP was added to 293 cells transfected with expression constructs for murine IL-7Rα, murine TSLPR, murine IL-7Rα and murine TSLPR, or human IL-7Rα and murine TSLPR, and then cross-linked with DSS.

As shown in FIG. 8A, $^{125}$I-TSLP bound to the heterodimer of murine IL-7Rα and murine TSLPR polypeptide (lane 4). The upper band corresponds to cross-linked murine IL-7Rα and the lower band corresponds to cross-linked murine TSLPR polypeptide. In addition, $^{125}$I-TSLP also bound the heterodimer of human IL-7Rα and murine TSLPR polypeptide (lane 5). No TSLP binding was observed with murine IL-7Rα alone (lane 2).

Affinity labeling assays were also performed using a FLAG-tagged version of murine TSLPR polypeptide, Murine TSLPR-FLAG polypeptide was derived by PCR amplifying a fragment containing the coding region of TSLPR polypeptide using a 3' primer containing sequence corresponding to the FLAG epitope. This PCR product was then subcloned into pCR3.1 (Invitrogen) and the resulting clone analyzed by sequencing. Affinity labeling assays were performed as described herein, with the exception that cell lysates were immunoprecipitated with an anti-FLAG monoclonal M2 antibody. As shown in FIG. 8B, following TSLPR immunoprecipitation, a cross-linked TSLPR band was observed (lane 1), indicating that TSLP exhibits weak binding to TSLPR alone.

To examine whether murine IL-7 could compete for TSLP binding in cells expressing TSLPR polypeptide and IL-7Rα, competition assays were performed. Cellular lysates were analyzed as described herein, with the exception that increasing amounts of unlabeled murine IL-7 were added with $^{125}$I-TSLP. As shown in FIG. 8C, an excess of murine IL-7 inhibited the binding of TSLP to the IL-7Rα/TSLPR polypeptide heterodimer. The affinity labeling assays illustrated the cooperativity of IL-7Rα and murine TSLPR polypeptide for binding TSLP. These assays also established that IL-7 can compete for the binding of TSLP, which has implications for potential competition between these two cytokines in vivo.

The binding of TSLP to 293 cells transfected with murine IL-7Rα and murine TSLPR polypeptide, or murine IL-7Rα alone, was analyzed in a displacement binding assay. Following two washes, 1×10$^6$ transfected 293 cells were incubated in a constant amount of $^{125}$I-labeled TSLP (approximately 20,000 cpm) and varying amounts of unlabeled TSLP. Following a 3 hour incubation, treated cells were separated from the medium by centrifugation in olive oil and N-butylphthalate. Cell-bound radioactivity was measured using a gamma counter.

Figure 9A:
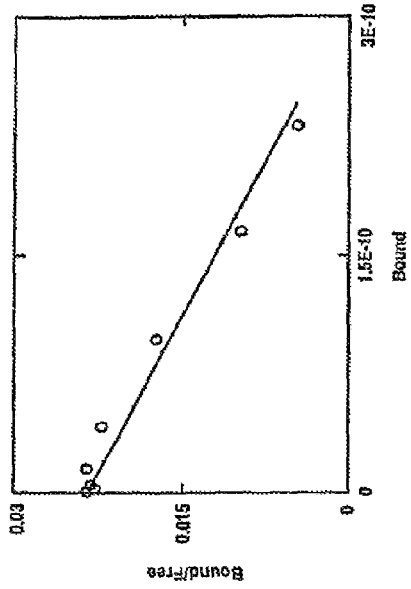
FIGS. 9A-9D illustrate the results obtained in displacement binding assays.
Figure 9B:
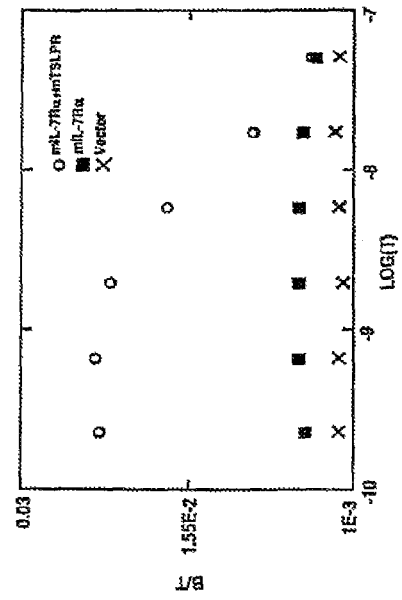
Figure 9D:
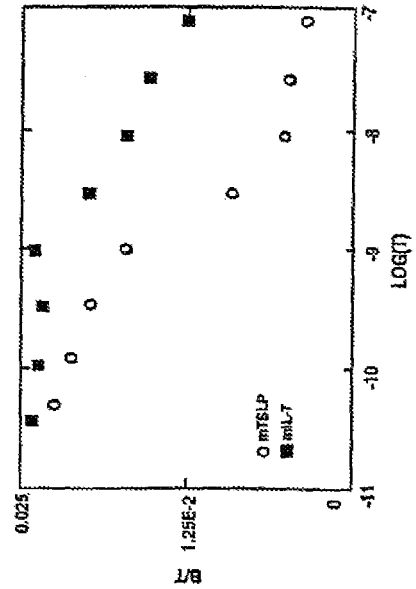
Figure 9C:
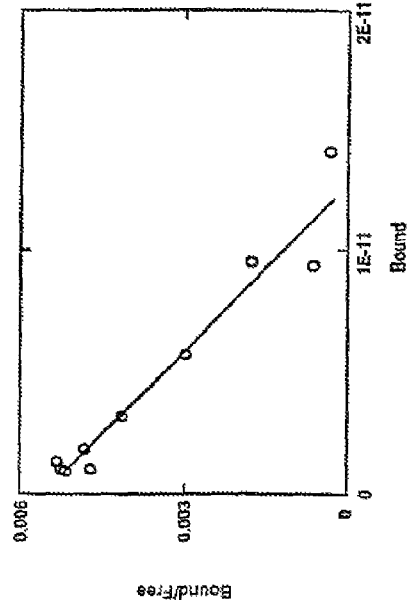

As shown in FIG. 9A, non-specific binding of $^{125}$I-TSLP was observed with cells transfected with murine IL-7Rα alone (or vector alone), while specific binding of $^{125}$I-TSLP was observed with cells transfected with both IL-7Rα and TSLPR polypeptide, with excess unlabeled TSLP competing for binding of $^{125}$I-TSLP. Cells transfected with TSLPR polypeptide alone exhibited very low binding. Analysis of binding data by Scatchard transformation was performed using the LIGAND computer program (Munson and Rodbard, 1980, *Anal. Biochem.* 107:220-39). The K$_d$ for the binding of TSLP to cells expressing TSLPR polypeptide and IL-7Rα was determined to be approximately 13 nM (FIG. 9B). In seven independent experiments, the K$_d$ was found to range from 1.2 to 40 nM. Due to the very low binding activity of TSLP for cells expressing TSLPR polypeptide alone, it was not possible to determine the K$_d$ for these cells. Displacement binding assays were also performed using NAG8/7 cells, which constitutively express TSLP receptors and proliferate in response to TSLP (Friend et al., supra; Levin et al., supra). In these displacement binding assays, 5×10$^6$ NAG8/7 cells were incubated in a constant amount of $^{125}$I-labeled TSLP (approximately 180,000 cpm) and varying amounts of unlabeled TSLP. The remainder of the assay was performed as described herein. As shown in FIG. 9C, the Scatchard transformation of binding data obtained using NAG8/7 cells suggested the cells expressed a single class of receptors having a K$_d$ of approximately 2.2 nM—results that are similar to those obtained using the transfected 293 cells.

Displacement binding assays were also performed to compare the displacement of $^{125}$I-labeled TSLP by IL-7 or unlabeled TSLP in 293 cells transfected with TSLPR polypeptide and IL-7Rα. FIG. 9D illustrates that murine IL-7 competes for binding to TSLPR polypeptide.

It has been previously shown that treatment of NAG8/7 cells with either IL-7 or TSLP activates STAT5 (Friend et al., supra; Levin et al., supra). The possible role of TSLPR polypeptide in STAT5 activation was analyzed in CAT assays using HepG2 cells. Expression constructs for IL-7Rα and TSLPR, or IL-7Rα and γ$_c$, were introduced into HepG2 cells with the pHRRE-CAT vector by calcium phosphate transfection. The pHRRE-CAT vector contains eight tandem copies of the 27 bp cytokine-inducible hematopoietin receptor response element and STAT5b (Ziegler et al., 1995, *Eur. J. Immunol.* 25:399-404). Transfected cells were allowed to recover overnight, after which the cells were trypsinized and plated in 6-well culture dishes. The cells were allowed to adhere to the plates during a 24 hour incubation, and the cells were then incubated with serum free medium containing 100 ng/ml of either IL-7 or TSLP, for an additional 24 hours.

Figure 10:
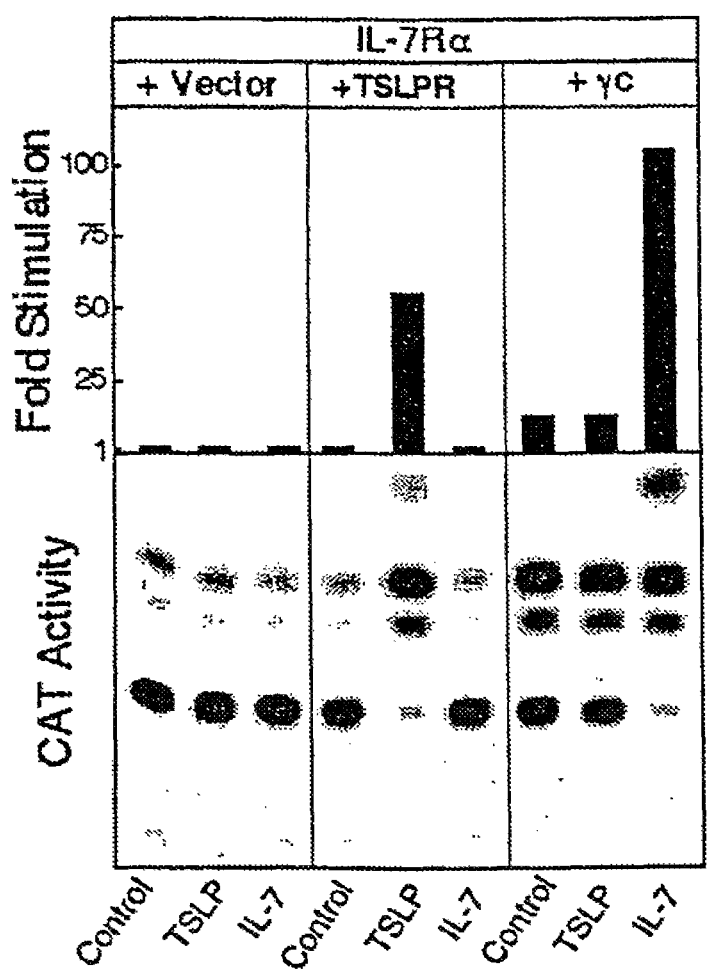
FIG. 10 illustrates the results obtained in CAT assays in which HepG2 cells were co-transfected with expression constructs for IL-7Rα and TSLPR, or $\gamma_c$, and pHRRE-CAT.

The CAT activity and fold stimulation alter normalizing for transfection efficiencies is shown in FIG. 10. No increase in CAT activity was seen after TSLP stimulation in the presence of IL-7Rα alone (lane 2) or with IL-7Rα and γ$_c$ (lane 7). However, if TSLPR polypeptide was co-transfected, a dramatic increase in CAT activity was observed following TSLP stimulation (lane 5). This demonstrates that the presence of TSLPR polypeptide is required for TSLP signaling. While co-transfection of γ$_c$ and IL-7Rα had no effect on TSLP-dependent reporter activity, this combination effectively mediated IL-7-dependent reporter activation (lane 9).

A number of cytokine receptor chains are shared by more than one cytokine. The best known examples are gp130, which is shared by IL-6, IL-11, ciliary neurotropic factor, leukemia inhibitory factor, oncostatin M, and cardiotrophin-1 (Hirano et al., 1997, *Cytokine Growth Factor Rev.* 8:241-52; Taga and Kishimoto, 1997, *Annu. Rev. Immunol.* 15:797-819), β$_c$, which is shared by IL-3, IL-5, and GM-CSF (Miyajima et al., 1997, *Leukemia* 11:418-22; Guthridge et al., 1998, *Stem Cells* 16:301-13; Burdach et al., 1998, *Curr. Opin. Hematol.* 5:177-80), and γ$_c$, which is shared by IL-2, IL-4, IL-7, IL-9, and IL-15 (Noguchi et al., 1993, *Science* 262:

1877-80; Kondo et al., 1994, supra; Kendo et al., 1993, supra; Russell et al., 1994, supra; Takeshita et al., supra; Russell et al., 1993, supra; Giri et al., supra; Kimura et al., supra). The list of cytokine receptor chains that serve as components of more than one cytokine receptor includes IL-2Rβ, which is a component of both the IL-2 and IL-15 receptors, and IL-4Rα, which is a component of both the IL-4 and IL-13 receptors. The cytokine receptor subunit IL-7Rα can now be added to this list as the data presented herein demonstrates that this subunit is a component of both the IL-7 and TSLP receptors.

The observation of defects in T-cell and B-cell development in Il7$^{-/-}$ mice (von Freeden-Jeffrey et al., 1995, *J. Exp. Med.* 181:1519-26) suggests that TSLP cannot fully compensate for the loss of IL-7. An examination of the functional cooperation of IL-7Rα in TSLP signaling may help to explain the differences in B-cell development in Il7r$^{-/-}$ and Il7$^{-/-}$ mice (Candeias et al., 1997, *Immunity* 6:501-08; von Freeden-Jeffrey et al., supra; Peschon et al., 1994, *J. Exp. Med.* 180:1955-60; He et al., 1997, *J. Immunol.* 158:2592-99). The further characterization of TSLPR polypeptide will aid this investigation.

EXAMPLE 5

Production of TSLPR Polypeptides

A. Expression of TSLPR Polypeptides in Bacteria

PCR is used to amplify template DNA sequences encoding a TSLPR polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC no. 98113) containing the lux promoter and a gene encoding kanamycin resistance is digested with Bam HI and Nde I for directional cloning of inserted DNA. The ligated mixture is transformed into an *E. coli* host strain by electroporation and transformants are selected for kanamycin resistance. Plasmid DNA from selected colonies is isolated and subjected to DNA sequencing to confirm the presence of the insert.

Transformed host cells are incubated in 2× YT medium containing 30 μg/mL kanamycin at 30° C. prior to induction. Gene expression is induced by the addition of N-(3-oxohexanoyl)-dl-homoserine lactone to a final concentration of 30 ng/mL followed by incubation at either 30° C. or 37° C. for six hours. The expression of TSLPR polypeptide is evaluated by centrifugation of the culture, resuspension and lysis of the bacterial pellets, and analysis of host cell proteins by SDS-polyacrylamide gel electrophoresis.

Inclusion bodies containing TSLPR polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 mL of a Percoll solution (75% liquid Percoll and 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to *E. coli*-produced TSLPR polypeptide is excised from the gel, and the N-terminal amino acid sequence is determined essentially as described by Matsudaira et al., 1987, *J. Biol. Chem.* 262:10-35.

B. Expression or TSLPR Polypeptide in Mammalian Cells

PCR is used to amplify template DNA sequences encoding a TSLPR polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen, Carlsbad, Calif.), that contains an Epstein-Barr virus origin of replication, may be used for the expression of TSLPR polypeptides in 293-EBNA-1 cells. Amplified and gel purified PCR products are ligated into pCEP4 vector and introduced into 293-EBNA cells by lipofection. The transfected cells are selected in 100 μg/mL hygromycin and the resulting drug-resistant cultures are grown to confluence. The cells are then cultured in serum-free media for 72 hours. The conditioned media is removed and TSLPR polypeptide expression is analyzed by SDS-PAGE.

TSLPR polypeptide expression may be detected by silver staining. Alternatively, TSLPR polypeptide is produced as a fusion protein with an epitope tag, such as an IgG constant domain or a FLAG epitope, which may be detected by Western blot analysis using antibodies to the peptide tag.

TSLPR polypeptides may be excised from an SDS-polyacrylamide gel, or TSLPR fusion proteins are purified by affinity chromatography to the epitope tag, and subjected to N-terminal amino acid sequence analysis as described herein.

C. Expression and Purification of TSLPR Polypeptide in Mammalian Cells

TSLPR polypeptide expression constructs are introduced into 293 EBNA or CHO cells using either a lipofection or calcium phosphate protocol.

To conduct functional studies on the TSLPR polypeptides that are produced, large quantities of conditioned media are generated from a pool of hygromycin selected 293 EBNA clones. The cells are cultured in 500 cm Nunc Triple Flasks to 80% confluence before switching to serum free media a week prior to harvesting the media. Conditioned media is harvested and frozen at −20° C. until purification.

Conditioned media is purified by affinity chromatography as described below. The media is thawed and then passed through a 0.2 μm filter. A Protein G column is equilibrated with PBS at pH 7.0, and then loaded with the filtered media. The column is washed with PBS until the absorbance at $A_{280}$ reaches a baseline, TSLPR polypeptide is eluted from the column with 0.1 M Glycined-HCl at pH 2.7 and immediately neutralized with 1 M Tris-HCl at pH 8.5. Fractions containing TSLPR polypeptide are pooled, dialyzed in PBS, and stored at −70° C.

For Factor Xa cleavage of the human TSLPR polypeptide-Fc fusion polypeptide, affinity chromatography-purified protein is dialyzed in 50 mM Tris-HCl, 100 mM NaCl, 2 mM $CaCl_2$ at pH 8.0. The restriction protease Factor Xa is added to the dialyzed protein at 1/100 (w/w) and the sample digested overnight at room temperature.

EXAMPLE 6

Production of Anti-TSLPR Polypeptide Antibodies

Antibodies to TSLPR polypeptides may be obtained by immunization with purified protein or with TSLPR peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a TSLPR antigen (such as a TSLPR polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 μg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-TSLPR antibody production by ELISA.

Alternative procedures for obtaining anti-TSLPR antibodies may also be employed, such as the immunization of transgenic mice harboring human Ig loci for production of human antibodies, and the screening of synthetic antibody libraries, such as those generated by mutagenesis of an antibody variable domain.

EXAMPLE 7

Expression of TSLPR Polypeptide in Transgenic Mice

To assess the biological activity of TSLPR polypeptide, a construct encoding a TSLPR polypeptide/Fc fusion protein under the control of a liver specific ApoE promoter is prepared. The delivery of this construct is expected to cause pathological changes that are informative as to the function of TSLPR polypeptide. Similarly, a construct containing the full-length TSLPR polypeptide under the control of the beta actin promoter is prepared. The delivery of this construct is expected to result in ubiquitous expression.

To generate these constructs, PCR is used to amplify template DNA sequences encoding a TSLPR polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified TSLPR polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The TSLPR polypeptide expression vector is purified through two rounds of CsCl density gradient centrifugation, cleaved with a suitable restriction enzyme, and the linearized fragment containing the TSLPR polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (PCT Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the Superscript™ Preamplification System (Gibco-BRL) as follows. A suitable primer, located in the expression vector sequence and 3' to the TSLPR polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of Superscript II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for TSLPR polypeptide.

Determining the phenotypes of $Tslp^{-/-}$ or $Tslpr^{-/-}$ mice will also assist in defining the exact role of TSLP.

EXAMPLE 8

Biological Activity of TSLPR Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed.

Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately 1×10⁶ cells from each tissue are then incubated for 10 minutes with 0.5 µg CD16/32(FcγIII/II) Fc block in a 20 µL volume. Samples are then stained for 30 minutes at 2-8° C. in a 100 µL volume of PBS (lacking Ca⁺ and Mg⁺), 0.1% bovine serum albumin, and 0.01% sodium azide with 0.5 µg antibody of FITC or PR-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method of blocking human thymic stromal lymphopoietin (TSLP) receptor activity, said method comprising contacting a cell expressing human TSLP receptor with an effective amount of an antibody or antigen-binding fragment thereof that specifically binds the extracellular domain of the TSLP receptor having the amino acid sequence set forth in SEQ ID NO:6 and blocks human TSLP binding to the amino acid sequence.

2. The method of claim 1, wherein the antibody is a monoclonal antibody.

3. The method of claim 1, wherein the antibody is a humanized antibody.

4. The method of claim 1, wherein the antibody is a human antibody.

5. The method of claim 1, wherein the method comprises contacting the cell with an antigen-binding fragment of the antibody.

6. The method of claim 1, wherein the antibody or antigen-binding fragment thereof is administered to a patient.

* * * * *

SEQUENCE LISTING

```
<160> NUMBER OF SEQ ID NOS: 16

<210> SEQ ID NO 1
<211> LENGTH: 1409
<212> TYPE: DNA
<213> ORGANISM: Mus musculus
<220> FEATURE:
<221> NAME/KEY: CDS
<222> LOCATION: (162)..(1274)
<220> FEATURE:
<221> NAME/KEY: sig_peptide
<222> LOCATION: (162)..(213)
<220> FEATURE:
<221> NAME/KEY: misc_feature
<222> LOCATION: (891)..(953)
<223> OTHER INFORMATION: Predicted transmembrane domain coding sequence

<400> SEQUENCE: 1 cccttcctc gccgacccct gaccccgccc cgccccgccc acccaggggc ccagacctga      60
gcggcggcca ggtcgcgggt gacgtcacag ggccgttgcc ccatccgtcc cgtggcctgg     120
acggacagag ctgaggcagg ggaataaccg cgagtgctga g atg gca tgg gca ctc    176
                                            Met Ala Trp Ala Leu
                                              1               5 gcg gtc atc ctc ctg cct cgg ctc ctt gcg gcg gca gcg gcg gcg gcg      224
Ala Val Ile Leu Leu Pro Arg Leu Leu Ala Ala Ala Ala Ala Ala
             10                  15                  20 gcg gtg acg tca cgg ggt gat gtc aca gtc gtc tgc cat gac ctg gag      272
Ala Val Thr Ser Arg Gly Asp Val Thr Val Val Cys His Asp Leu Glu
         25                  30                  35 acg gtg gag gtc acg tgg ggc tcg ggc ccc gac cac cac agc gcc aac      320
Thr Val Glu Val Thr Trp Gly Ser Gly Pro Asp His His Ser Ala Asn
     40                  45                  50 ttg agc ctg gag ttc cgt tat ggt act ggc gcc ctg caa ccc tgc ccg      368
Leu Ser Leu Glu Phe Arg Tyr Gly Thr Gly Ala Leu Gln Pro Cys Pro
 55                  60                  65 cga tat ttc ctg tcc ggc gct ggt gtc act tcc ggg tgc atc ctc ccc      416
Arg Tyr Phe Leu Ser Gly Ala Gly Val Thr Ser Gly Cys Ile Leu Pro
70                  75                  80                  85 gcg gcg agg gcg ggg ctg ctg gag ctg gca ctg cgc gac gga ggc ggg      464
Ala Ala Arg Ala Gly Leu Leu Glu Leu Ala Leu Arg Asp Gly Gly Gly
                 90                  95                 100 gcc atg gtg ttt aag gct agg cag cgc gcg tcc gcg tgg ctg aag ccc      512
Ala Met Val Phe Lys Ala Arg Gln Arg Ala Ser Ala Trp Leu Lys Pro
            105                 110                 115 cgc cca cct tgg aat gtg acg ctg ctc tgg aca cca gac ggg gac gtg      560
Arg Pro Pro Trp Asn Val Thr Leu Leu Trp Thr Pro Asp Gly Asp Val
        120                 125                 130 act gtc tcc tgg cct gcc cac tcc tac ctg ggc ctg gac tac gag gtg      608
Thr Val Ser Trp Pro Ala His Ser Tyr Leu Gly Leu Asp Tyr Glu Val
    135                 140                 145 cag cac cgg gag agc aat gac gat gag gac gcc tgg cag acg acc tca      656
Gln His Arg Glu Ser Asn Asp Asp Glu Asp Ala Trp Gln Thr Thr Ser
```

-continued

| | | | | | | | | | | | | | | | | |
|---|---|---|---|---|---|---|---|---|---|---|---|---|---|---|---|---|
| | | 150 | | | | 155 | | | | 160 | | | | 165 | | |
| ggg | ccc | tgc | tgt | gac | ttg | aca | gtg | ggc | ggg | ctc | gac | ccc | gcg | cgc | tgc | 704 |
| Gly | Pro | Cys | Cys | Asp | Leu | Thr | Val | Gly | Gly | Leu | Asp | Pro | Ala | Arg | Cys | |
| | | | | 170 | | | | 175 | | | | 180 | | | | |
| tat | gac | ttc | cgg | gtt | cgg | gcg | tcg | ccc | cgg | gcc | gcg | cac | tat | ggc | ctg | 752 |
| Tyr | Asp | Phe | Arg | Val | Arg | Ala | Ser | Pro | Arg | Ala | Ala | His | Tyr | Gly | Leu | |
| | | | 185 | | | | 190 | | | | 195 | | | | | |
| gag | gcg | cag | cct | agc | gag | tgg | aca | gcg | gtg | aca | agg | ctt | tcc | ggg | gca | 800 |
| Glu | Ala | Gln | Pro | Ser | Glu | Trp | Thr | Ala | Val | Thr | Arg | Leu | Ser | Gly | Ala | |
| | | 200 | | | | 205 | | | | 210 | | | | | | |
| gca | tcc | gcg | ggt | gac | ccc | tgc | gcc | gcc | cac | ctt | ccc | ccc | cta | gcc | tcc | 848 |
| Ala | Ser | Ala | Gly | Asp | Pro | Cys | Ala | Ala | His | Leu | Pro | Pro | Leu | Ala | Ser | |
| | 215 | | | | 220 | | | | 225 | | | | | | | |
| tgt | acc | gca | agc | ccc | gcc | cca | tcc | ccg | gcc | ctg | gcc | ccg | ccc | ctc | ctg | 896 |
| Cys | Thr | Ala | Ser | Pro | Ala | Pro | Ser | Pro | Ala | Leu | Ala | Pro | Pro | Leu | Leu | |
| 230 | | | | 235 | | | | 240 | | | | 245 | | | | |
| ccc | ctg | ggc | tgc | ggc | cta | gca | gcg | ctg | ctg | aca | ctg | tcc | ctg | ctc | ctg | 944 |
| Pro | Leu | Gly | Cys | Gly | Leu | Ala | Ala | Leu | Leu | Thr | Leu | Ser | Leu | Leu | Leu | |
| | | | 250 | | | | 255 | | | | 260 | | | | | |
| gcc | gcc | ctg | agg | ctt | cgc | agg | gtg | aaa | gat | gcg | ctg | ctg | ccc | tgc | gtc | 992 |
| Ala | Ala | Leu | Arg | Leu | Arg | Arg | Val | Lys | Asp | Ala | Leu | Leu | Pro | Cys | Val | |
| | | 265 | | | | 270 | | | | 275 | | | | | | |
| cct | gac | ccc | agc | ggc | tcc | ttc | cct | gga | ctc | ttt | gag | aag | cat | cac | ggg | 1040 |
| Pro | Asp | Pro | Ser | Gly | Ser | Phe | Pro | Gly | Leu | Phe | Glu | Lys | His | His | Gly | |
| | 280 | | | | 285 | | | | 290 | | | | | | | |
| aac | ttc | cag | gcc | tgg | att | gcg | gac | gcc | cag | gcc | aca | gcc | ccg | cca | gcc | 1088 |
| Asn | Phe | Gln | Ala | Trp | Ile | Ala | Asp | Ala | Gln | Ala | Thr | Ala | Pro | Pro | Ala | |
| 295 | | | | 300 | | | | 305 | | | | | | | | |
| agg | acc | gag | gag | gaa | gat | gac | ctc | atc | cac | ccc | aag | gct | aag | agg | gtg | 1136 |
| Arg | Thr | Glu | Glu | Glu | Asp | Asp | Leu | Ile | His | Pro | Lys | Ala | Lys | Arg | Val | |
| 310 | | | | 315 | | | | 320 | | | | 325 | | | | |
| gag | ccc | gag | gat | ggc | acc | tcc | ctc | tgc | acc | gtg | cca | agg | cca | ccc | agc | 1184 |
| Glu | Pro | Glu | Asp | Gly | Thr | Ser | Leu | Cys | Thr | Val | Pro | Arg | Pro | Pro | Ser | |
| | | | 330 | | | | 335 | | | | 340 | | | | | |
| ttc | gag | cca | agg | ggg | ccg | gga | ggc | ggg | gcc | atg | gtg | tca | gtg | ggc | ggg | 1232 |
| Phe | Glu | Pro | Arg | Gly | Pro | Gly | Gly | Gly | Ala | Met | Val | Ser | Val | Gly | Gly | |
| | | 345 | | | | 350 | | | | 355 | | | | | | |
| gcc | acg | ttc | atg | gtg | ggc | gac | agc | ggc | tac | atg | acc | ctg | tga | | | 1274 |
| Ala | Thr | Phe | Met | Val | Gly | Asp | Ser | Gly | Tyr | Met | Thr | Leu | | | | |
| | 360 | | | | 365 | | | | 370 | | | | | | | | ccttgaagtc actgccagtc tatacttcag gctgaggtca cttcctgtct ttaaataatt    1334 caaactcaca aatcctgtgc ctgtctgtat gcaaatgtgg tcacgaatat tcaaataaaa    1394 tgcaaatgct atgct    1409

<210> SEQ ID NO 2
<211> LENGTH: 370
<212> TYPE: PRT
<213> ORGANISM: Mus musculus

<400> SEQUENCE: 2

Met Ala Trp Ala Leu Ala Val Ile Leu Leu Pro Arg Leu Leu Ala
1               5                   10                  15

Ala Ala Ala Ala Ala Val Thr Ser Arg Gly Asp Val Thr Val Val
                20                  25                  30

Cys His Asp Leu Glu Thr Val Glu Val Thr Trp Gly Ser Gly Pro Asp
            35                  40                  45

His His Ser Ala Asn Leu Ser Leu Glu Phe Arg Tyr Gly Thr Gly Ala
        50                  55                  60

```
Leu Gln Pro Cys Pro Arg Tyr Phe Leu Ser Gly Ala Gly Val Thr Ser
 65                  70                  75                  80

Gly Cys Ile Leu Pro Ala Ala Arg Ala Gly Leu Leu Glu Leu Ala Leu
                 85                  90                  95

Arg Asp Gly Gly Gly Ala Met Val Phe Lys Ala Arg Gln Arg Ala Ser
            100                 105                 110

Ala Trp Leu Lys Pro Arg Pro Trp Asn Val Thr Leu Leu Trp Thr
        115                 120                 125

Pro Asp Gly Asp Val Thr Val Ser Trp Pro Ala His Ser Tyr Leu Gly
        130                 135                 140

Leu Asp Tyr Glu Val Gln His Arg Glu Ser Asn Asp Glu Asp Ala
145                 150                 155                 160

Trp Gln Thr Thr Ser Gly Pro Cys Cys Asp Leu Thr Val Gly Gly Leu
                165                 170                 175

Asp Pro Ala Arg Cys Tyr Asp Phe Arg Val Arg Ala Ser Pro Arg Ala
            180                 185                 190

Ala His Tyr Gly Leu Glu Ala Gln Pro Ser Glu Trp Thr Ala Val Thr
        195                 200                 205

Arg Leu Ser Gly Ala Ala Ser Ala Gly Asp Pro Cys Ala Ala His Leu
210                 215                 220

Pro Pro Leu Ala Ser Cys Thr Ala Ser Pro Ala Pro Ser Pro Ala Leu
225                 230                 235                 240

Ala Pro Pro Leu Leu Pro Leu Gly Cys Gly Leu Ala Ala Leu Leu Thr
                245                 250                 255

Leu Ser Leu Leu Leu Ala Ala Leu Leu Arg Arg Val Lys Asp Ala
            260                 265                 270

Leu Leu Pro Cys Val Pro Asp Pro Ser Gly Ser Phe Pro Gly Leu Phe
        275                 280                 285

Glu Lys His His Gly Asn Phe Gln Ala Trp Ile Ala Asp Ala Gln Ala
        290                 295                 300

Thr Ala Pro Pro Ala Arg Thr Glu Glu Asp Asp Leu Ile His Pro
305                 310                 315                 320

Lys Ala Lys Arg Val Glu Pro Glu Asp Gly Thr Ser Leu Cys Thr Val
                325                 330                 335

Pro Arg Pro Pro Ser Phe Glu Pro Arg Gly Pro Gly Gly Ala Met
            340                 345                 350

Val Ser Val Gly Gly Ala Thr Phe Met Val Gly Asp Ser Gly Tyr Met
        355                 360                 365

Thr Leu
    370

<210> SEQ ID NO 3
<211> LENGTH: 353
<212> TYPE: PRT
<213> ORGANISM: Mus musculus
<220> FEATURE:
<221> NAME/KEY: TRANSMEM
<222> LOCATION: (227)..(247)

<400> SEQUENCE: 3

Ala Ala Ala Ala Ala Val Thr Ser Arg Gly Asp Val Thr Val Val Cys
1               5                  10                  15

His Asp Leu Glu Thr Val Glu Val Thr Trp Gly Ser Gly Pro Asp His
            20                  25                  30

His Ser Ala Asn Leu Ser Leu Glu Phe Arg Tyr Gly Thr Gly Ala Leu
```

```
                    35                  40                  45
Gln Pro Cys Pro Arg Tyr Phe Leu Ser Gly Ala Gly Val Thr Ser Gly
 50                  55                  60

Cys Ile Leu Pro Ala Ala Arg Ala Gly Leu Leu Glu Leu Ala Leu Arg
 65                  70                  75                  80

Asp Gly Gly Gly Ala Met Val Phe Lys Ala Arg Gln Arg Ala Ser Ala
                 85                  90                  95

Trp Leu Lys Pro Arg Pro Pro Trp Asn Val Thr Leu Leu Trp Thr Pro
                100                 105                 110

Asp Gly Asp Val Thr Val Ser Trp Pro Ala His Ser Tyr Leu Gly Leu
                115                 120                 125

Asp Tyr Glu Val Gln His Arg Glu Ser Asn Asp Asp Glu Asp Ala Trp
                130                 135                 140

Gln Thr Thr Ser Gly Pro Cys Cys Asp Leu Thr Val Gly Gly Leu Asp
145                 150                 155                 160

Pro Ala Arg Cys Tyr Asp Phe Arg Val Arg Ala Ser Pro Arg Ala Ala
                165                 170                 175

His Tyr Gly Leu Glu Ala Gln Pro Ser Glu Trp Thr Ala Val Thr Arg
                180                 185                 190

Leu Ser Gly Ala Ala Ser Ala Gly Asp Pro Cys Ala Ala His Leu Pro
                195                 200                 205

Pro Leu Ala Ser Cys Thr Ala Ser Pro Ala Pro Ser Pro Ala Leu Ala
210                 215                 220

Pro Pro Leu Leu Pro Leu Gly Cys Gly Leu Ala Ala Leu Leu Thr Leu
225                 230                 235                 240

Ser Leu Leu Leu Ala Ala Leu Arg Leu Arg Arg Val Lys Asp Ala Leu
                245                 250                 255

Leu Pro Cys Val Pro Asp Pro Ser Gly Ser Phe Pro Gly Leu Phe Glu
                260                 265                 270

Lys His His Gly Asn Phe Gln Ala Trp Ile Ala Asp Ala Gln Ala Thr
                275                 280                 285

Ala Pro Pro Ala Arg Thr Glu Glu Glu Asp Asp Leu Ile His Pro Lys
290                 295                 300

Ala Lys Arg Val Glu Pro Glu Asp Gly Thr Ser Leu Cys Thr Val Pro
305                 310                 315                 320

Arg Pro Pro Ser Phe Glu Pro Arg Gly Pro Gly Gly Gly Ala Met Val
                325                 330                 335

Ser Val Gly Gly Ala Thr Phe Met Val Gly Asp Ser Gly Tyr Met Thr
                340                 345                 350

Leu

<210> SEQ ID NO 4
<211> LENGTH: 1116
<212> TYPE: DNA
<213> ORGANISM: Homo sapiens
<220> FEATURE:
<221> NAME/KEY: CDS
<222> LOCATION: (1)..(1116)
<220> FEATURE:
<221> NAME/KEY: sig_peptide
<222> LOCATION: (1)..(66)
<220> FEATURE:
<221> NAME/KEY: misc_feature
<222> LOCATION: (694)..(756)
<223> OTHER INFORMATION: Predicted transmembrane domain coding sequence

<400> SEQUENCE: 4
```

| | | |
|---|---|---|
| atg ggg cgg ctg gtt ctg ctg tgg gga gct gcc gtc ttt ctg ctg gga<br>Met Gly Arg Leu Val Leu Leu Trp Gly Ala Ala Val Phe Leu Leu Gly<br>1               5                   10                  15 | 48 |
| ggc tgg atg gct ttg ggg caa gga gga gca gca gaa gga gta cag att<br>Gly Trp Met Ala Leu Gly Gln Gly Gly Ala Ala Glu Gly Val Gln Ile<br>        20                  25                  30 | 96 |
| cag atc atc tac ttc aat tta gaa acc gtg cag gtg aca tgg aat gcc<br>Gln Ile Ile Tyr Phe Asn Leu Glu Thr Val Gln Val Thr Trp Asn Ala<br>    35                  40                  45 | 144 |
| agc aaa tac tcc agg acc aac ctg act ttc cac tac aga ttc aac ggt<br>Ser Lys Tyr Ser Arg Thr Asn Leu Thr Phe His Tyr Arg Phe Asn Gly<br>50                  55                  60 | 192 |
| gat gag gcc tat gac cag tgc acc aac tac ctt ctc cag gaa ggt cac<br>Asp Glu Ala Tyr Asp Gln Cys Thr Asn Tyr Leu Leu Gln Glu Gly His<br>65              70                  75                  80 | 240 |
| act tca ggg tgc ctc cta gac gca gag cag cga gac gac att ctc tat<br>Thr Ser Gly Cys Leu Leu Asp Ala Glu Gln Arg Asp Asp Ile Leu Tyr<br>            85                  90                  95 | 288 |
| ttc tcc atc agg aat ggg acg cac ccc gtt ttc acc gca agt cgc tgg<br>Phe Ser Ile Arg Asn Gly Thr His Pro Val Phe Thr Ala Ser Arg Trp<br>                100                 105                 110 | 336 |
| atg gtt tat tac ctg aaa ccc agt tcc ccg aag cac gtg aga ttt tcg<br>Met Val Tyr Tyr Leu Lys Pro Ser Ser Pro Lys His Val Arg Phe Ser<br>            115                 120                 125 | 384 |
| tgg cat cag gat gca gtg acg gtg acg tgt tct gac ctg tcc tac ggg<br>Trp His Gln Asp Ala Val Thr Val Thr Cys Ser Asp Leu Ser Tyr Gly<br>        130                 135                 140 | 432 |
| gat ctc ctc tat gag gtt cag tac cgg agc ccc ttc gac acc gag tgg<br>Asp Leu Leu Tyr Glu Val Gln Tyr Arg Ser Pro Phe Asp Thr Glu Trp<br>145                 150                 155                 160 | 480 |
| cag tcc aaa cag gaa aat acc tgc aac gtc acc ata gaa ggc ttg gat<br>Gln Ser Lys Gln Glu Asn Thr Cys Asn Val Thr Ile Glu Gly Leu Asp<br>                165                 170                 175 | 528 |
| gcc gag aag tgt tac tct ttc tgg gtc agg gtg aag gct atg gag gat<br>Ala Glu Lys Cys Tyr Ser Phe Trp Val Arg Val Lys Ala Met Glu Asp<br>            180                 185                 190 | 576 |
| gta tat ggg cca gac aca tac cca agc gac tgg tca gag gtg aca tgc<br>Val Tyr Gly Pro Asp Thr Tyr Pro Ser Asp Trp Ser Glu Val Thr Cys<br>        195                 200                 205 | 624 |
| tgg cag aga ggc gag att cgg gat gcc tgt gca gag aca cca acg cct<br>Trp Gln Arg Gly Glu Ile Arg Asp Ala Cys Ala Glu Thr Pro Thr Pro<br>    210                 215                 220 | 672 |
| ccc aaa cca aag ctg tcc aaa ttt att tta att tcc agc ctg gcc atc<br>Pro Lys Pro Lys Leu Ser Lys Phe Ile Leu Ile Ser Ser Leu Ala Ile<br>225                 230                 235                 240 | 720 |
| ctt ctg atg gtg tct ctc ctc ttg ctg tct tta tgg aaa tta tgg aga<br>Leu Leu Met Val Ser Leu Leu Leu Leu Ser Leu Trp Lys Leu Trp Arg<br>                245                 250                 255 | 768 |
| gtg aag aag ttt ctc att ccc agc gtg cca gac ccg aaa tcc atc ttc<br>Val Lys Lys Phe Leu Ile Pro Ser Val Pro Asp Pro Lys Ser Ile Phe<br>            260                 265                 270 | 816 |
| ccc ggg ctc ttt gag ata cac caa ggg aac ttc cag gag tgg atc aca<br>Pro Gly Leu Phe Glu Ile His Gln Gly Asn Phe Gln Glu Trp Ile Thr<br>        275                 280                 285 | 864 |
| gac acc cag aac gtg gcc cac ctc cac aag atg gca ggt gca gag caa<br>Asp Thr Gln Asn Val Ala His Leu His Lys Met Ala Gly Ala Glu Gln<br>    290                 295                 300 | 912 |
| gaa agt ggc ccc gag gag ccc ctg gta gtc cag ttg gcc aag act gaa<br>Glu Ser Gly Pro Glu Glu Pro Leu Val Val Gln Leu Ala Lys Thr Glu<br>305                 310                 315                 320 | 960 |

-continued

| | | | | | | | | | | | | |
|---|---|---|---|---|---|---|---|---|---|---|---|---|
| gcc | gag | tct | ccc | agg | atg | ctg | gac | cca | cag | acc | gag | gag | aaa | gag | gcc | 1008 |
| Ala | Glu | Ser | Pro | Arg | Met | Leu | Asp | Pro | Gln | Thr | Glu | Glu | Lys | Glu | Ala | |
| | | | 325 | | | | | 330 | | | | | 335 | | | |

```
gcc gag tct ccc agg atg ctg gac cca cag acc gag gag aaa gag gcc       1008
Ala Glu Ser Pro Arg Met Leu Asp Pro Gln Thr Glu Glu Lys Glu Ala
            325                 330                 335 tct ggg gga tcc ctc cag ctt ccc cac cag ccc ctc caa ggc ggt gat       1056
Ser Gly Gly Ser Leu Gln Leu Pro His Gln Pro Leu Gln Gly Gly Asp
            340                 345                 350 gtg gtc aca atc ggg ggc ttc acc ttt gtg atg aat gac cgc tcc tac       1104
Val Val Thr Ile Gly Gly Phe Thr Phe Val Met Asn Asp Arg Ser Tyr
            355                 360                 365 gtg gcg ttg tga                                                       1116
Val Ala Leu
    370

<210> SEQ ID NO 5
<211> LENGTH: 371
<212> TYPE: PRT
<213> ORGANISM: Homo sapiens

<400> SEQUENCE: 5

Met Gly Arg Leu Val Leu Leu Trp Gly Ala Ala Val Phe Leu Leu Gly
1               5                   10                  15

Gly Trp Met Ala Leu Gly Gln Gly Gly Ala Ala Glu Gly Val Gln Ile
                20                  25                  30

Gln Ile Ile Tyr Phe Asn Leu Glu Thr Val Gln Val Thr Trp Asn Ala
            35                  40                  45

Ser Lys Tyr Ser Arg Thr Asn Leu Thr Phe His Tyr Arg Phe Asn Gly
        50                  55                  60

Asp Glu Ala Tyr Asp Gln Cys Thr Asn Tyr Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
            100                 105                 110

Met Val Tyr Tyr Leu Lys Pro Ser Ser Pro Lys His Val Arg Phe Ser
        115                 120                 125

Trp His Gln Asp Ala Val Thr Val Thr Cys Ser Asp Leu Ser Tyr Gly
    130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Val Thr Cys
        195                 200                 205

Trp Gln Arg Gly Glu Ile Arg Asp Ala Cys Ala Glu Thr Pro Thr Pro
    210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
            260                 265                 270

Pro Gly Leu Phe Glu Ile His Gln Gly Asn Phe Gln Glu Trp Ile Thr
        275                 280                 285
```

```
Asp Thr Gln Asn Val Ala His Leu His Lys Met Ala Gly Ala Glu Gln
            290                 295                 300

Glu Ser Gly Pro Glu Glu Pro Leu Val Val Gln Leu Ala Lys Thr Glu
305                 310                 315                 320

Ala Glu Ser Pro Arg Met Leu Asp Pro Gln Thr Glu Glu Lys Glu Ala
                325                 330                 335

Ser Gly Gly Ser Leu Gln Leu Pro His Gln Pro Leu Gln Gly Gly Asp
                340                 345                 350

Val Val Thr Ile Gly Gly Phe Thr Phe Val Met Asn Asp Arg Ser Tyr
                355                 360                 365

Val Ala Leu
    370

<210> SEQ ID NO 6
<211> LENGTH: 349
<212> TYPE: PRT
<213> ORGANISM: Homo sapiens
<220> FEATURE:
<221> NAME/KEY: TRANSMEM
<222> LOCATION: (210)..(230)

<400> SEQUENCE: 6

Gln Gly Gly Ala Ala Glu Gly Val Gln Ile Gln Ile Ile Tyr Phe Asn
1               5                   10                  15

Leu Glu Thr Val Gln Val Thr Trp Asn Ala Ser Lys Tyr Ser Arg Thr
                20                  25                  30

Asn Leu Thr Phe His Tyr Arg Phe Asn Gly Asp Glu Ala Tyr Asp Gln
                35                  40                  45

Cys Thr Asn Tyr Leu Leu Gln Glu Gly His Thr Ser Gly Cys Leu Leu
    50                  55                  60

Asp Ala Glu Gln Arg Asp Asp Ile Leu Tyr Phe Ser Ile Arg Asn Gly
65                  70                  75                  80

Thr His Pro Val Phe Thr Ala Ser Arg Trp Met Val Tyr Tyr Leu Lys
                85                  90                  95

Pro Ser Ser Pro Lys His Val Arg Phe Ser Trp His Gln Asp Ala Val
                100                 105                 110

Thr Val Thr Cys Ser Asp Leu Ser Tyr Gly Asp Leu Leu Tyr Glu Val
            115                 120                 125

Gln Tyr Arg Ser Pro Phe Asp Thr Glu Trp Gln Ser Lys Gln Glu Asn
        130                 135                 140

Thr Cys Asn Val Thr Ile Glu Gly Leu Asp Ala Glu Lys Cys Tyr Ser
145                 150                 155                 160

Phe Trp Val Arg Val Lys Ala Met Glu Asp Val Tyr Gly Pro Asp Thr
                165                 170                 175

Tyr Pro Ser Asp Trp Ser Glu Val Thr Cys Trp Gln Arg Gly Glu Ile
                180                 185                 190

Arg Asp Ala Cys Ala Glu Thr Pro Thr Pro Lys Pro Lys Leu Ser
                195                 200                 205

Lys Phe Ile Leu Ile Ser Ser Leu Ala Ile Leu Leu Met Val Ser Leu
210                 215                 220

Leu Leu Leu Ser Leu Trp Lys Leu Trp Arg Val Lys Lys Phe Leu Ile
225                 230                 235                 240

Pro Ser Val Pro Asp Pro Lys Ser Ile Phe Pro Gly Leu Phe Glu Ile
                245                 250                 255

His Gln Gly Asn Phe Gln Glu Trp Ile Thr Asp Thr Gln Asn Val Ala
                260                 265                 270
```

```
His Leu His Lys Met Ala Gly Ala Glu Gln Glu Ser Gly Pro Glu Glu
        275                 280                 285

Pro Leu Val Val Gln Leu Ala Lys Thr Glu Ala Glu Ser Pro Arg Met
        290                 295                 300

Leu Asp Pro Gln Thr Glu Glu Lys Glu Ala Ser Gly Gly Ser Leu Gln
305                 310                 315                 320

Leu Pro His Gln Pro Leu Gln Gly Gly Asp Val Val Thr Ile Gly Gly
                325                 330                 335

Phe Thr Phe Val Met Asn Asp Arg Ser Tyr Val Ala Leu
            340                 345
```

<210> SEQ ID NO 7
<211> LENGTH: 1140
<212> TYPE: DNA
<213> ORGANISM: Artificial Sequence
<220> FEATURE:
<223> OTHER INFORMATION: Description of Artificial Sequence: Human
      TSLPR-FLAG
<220> FEATURE:
<221> NAME/KEY: CDS
<222> LOCATION: (1)..(1140)
<220> FEATURE:
<221> NAME/KEY: sig_peptide
<222> LOCATION: (1)..(66)
<220> FEATURE:
<221> NAME/KEY: misc_feature
<222> LOCATION: (694)..(756)
<223> OTHER INFORMATION: Predicted transmembrane domain coding sequence
<220> FEATURE:
<221> NAME/KEY: misc_feature
<222> LOCATION: (1114)..(1140)
<223> OTHER INFORMATION: FLAG coding sequence

<400> SEQUENCE: 7

```
atg ggg cgg ctg gtt ctg ctg tgg gga gct gcc gtc ttt ctg ctg gga         48
Met Gly Arg Leu Val Leu Leu Trp Gly Ala Ala Val Phe Leu Leu Gly
1               5                   10                  15 ggc tgg atg gct ttg ggg caa gga gga gca gca gaa gga gta cag att         96
Gly Trp Met Ala Leu Gly Gln Gly Gly Ala Ala Glu Gly Val Gln Ile
            20                  25                  30 cag atc atc tac ttc aat tta gaa acc gtg cag gtg aca tgg aat gcc        144
Gln Ile Ile Tyr Phe Asn Leu Glu Thr Val Gln Val Thr Trp Asn Ala
        35                  40                  45 agc aaa tac tcc agg acc aac ctg act ttc cac tac aga ttc aac ggt        192
Ser Lys Tyr Ser Arg Thr Asn Leu Thr Phe His Tyr Arg Phe Asn Gly
    50                  55                  60 gat gag gcc tat gac cag tgc acc aac tac ctt ctc cag gaa ggt cac        240
Asp Glu Ala Tyr Asp Gln Cys Thr Asn Tyr Leu Leu Gln Glu Gly His
65                  70                  75                  80 act tca ggg tgc ctc cta gac gca gag cag cga gac gac att ctc tat        288
Thr Ser Gly Cys Leu Leu Asp Ala Glu Gln Arg Asp Asp Ile Leu Tyr
                85                  90                  95 ttc tcc atc agg aat ggg acg cac ccc gtt ttc acc gca agt cgc tgg        336
Phe Ser Ile Arg Asn Gly Thr His Pro Val Phe Thr Ala Ser Arg Trp
            100                 105                 110 atg gtt tat tac ctg aaa ccc agt tcc ccg aag cac gtg aga ttt tcg        384
Met Val Tyr Tyr Leu Lys Pro Ser Ser Pro Lys His Val Arg Phe Ser
        115                 120                 125 tgg cat cag gat gca gtg acg gtg acg tgt tct gac ctg tcc tac ggg        432
Trp His Gln Asp Ala Val Thr Val Thr Cys Ser Asp Leu Ser Tyr Gly
    130                 135                 140 gat ctc ctc tat gag gtt cag tac cgg agc ccc ttc gac acc gag tgg        480
Asp Leu Leu Tyr Glu Val Gln Tyr Arg Ser Pro Phe Asp Thr Glu Trp
```

| | | | | | | | | | | | | | | | | |
|---|---|---|---|---|---|---|---|---|---|---|---|---|---|---|---|---|
| 145 | | | | 150 | | | | 155 | | | | 160 | | | | |
| cag | tcc | aaa | cag | gaa | aat | acc | tgc | aac | gtc | acc | ata | gaa | ggc | ttg | gat | 528 |
| Gln | Ser | Lys | Gln | Glu | Asn | Thr | Cys | Asn | Val | Thr | Ile | Glu | Gly | Leu | Asp | |
| | | | | 165 | | | | | 170 | | | | | 175 | | |
| gcc | gag | aag | tgt | tac | tct | ttc | tgg | gtc | agg | gtg | aag | gct | atg | gag | gat | 576 |
| Ala | Glu | Lys | Cys | Tyr | Ser | Phe | Trp | Val | Arg | Val | Lys | Ala | Met | Glu | Asp | |
| | | | 180 | | | | | 185 | | | | | 190 | | | |
| gta | tat | ggg | cca | gac | aca | tac | cca | agc | gac | tgg | tca | gag | gtg | aca | tgc | 624 |
| Val | Tyr | Gly | Pro | Asp | Thr | Tyr | Pro | Ser | Asp | Trp | Ser | Glu | Val | Thr | Cys | |
| | | 195 | | | | | 200 | | | | | 205 | | | | |
| tgg | cag | aga | ggc | gag | att | cgg | gat | gcc | tgt | gca | gag | aca | cca | acg | cct | 672 |
| Trp | Gln | Arg | Gly | Glu | Ile | Arg | Asp | Ala | Cys | Ala | Glu | Thr | Pro | Thr | Pro | |
| | 210 | | | | | 215 | | | | | 220 | | | | | |
| ccc | aaa | cca | aag | ctg | tcc | aaa | ttt | att | tta | att | tcc | agc | ctg | gcc | atc | 720 |
| Pro | Lys | Pro | Lys | Leu | Ser | Lys | Phe | Ile | Leu | Ile | Ser | Ser | Leu | Ala | Ile | |
| 225 | | | | | 230 | | | | | 235 | | | | | 240 | |
| ctt | ctg | atg | gtg | tct | ctc | ctc | ctt | ctg | tct | tta | tgg | aaa | tta | tgg | aga | 768 |
| Leu | Leu | Met | Val | Ser | Leu | Leu | Leu | Leu | Ser | Leu | Trp | Lys | Leu | Trp | Arg | |
| | | | | 245 | | | | | 250 | | | | | 255 | | |
| gtg | aag | aag | ttt | ctc | att | ccc | agc | gtg | cca | gac | ccg | aaa | tcc | atc | ttc | 816 |
| Val | Lys | Lys | Phe | Leu | Ile | Pro | Ser | Val | Pro | Asp | Pro | Lys | Ser | Ile | Phe | |
| | | | 260 | | | | | 265 | | | | | 270 | | | |
| ccc | ggg | ctc | ttt | gag | ata | cac | caa | ggg | aac | ttc | cag | gag | tgg | atc | aca | 864 |
| Pro | Gly | Leu | Phe | Glu | Ile | His | Gln | Gly | Asn | Phe | Gln | Glu | Trp | Ile | Thr | |
| | | 275 | | | | | 280 | | | | | 285 | | | | |
| gac | acc | cag | aac | gtg | gcc | cac | ctc | cac | aag | atg | gca | ggt | gca | gag | caa | 912 |
| Asp | Thr | Gln | Asn | Val | Ala | His | Leu | His | Lys | Met | Ala | Gly | Ala | Glu | Gln | |
| | 290 | | | | | 295 | | | | | 300 | | | | | |
| gaa | agt | ggc | ccc | gag | gag | ccc | ctg | gta | gtc | cag | ttg | gcc | aag | act | gaa | 960 |
| Glu | Ser | Gly | Pro | Glu | Glu | Pro | Leu | Val | Val | Gln | Leu | Ala | Lys | Thr | Glu | |
| 305 | | | | | 310 | | | | | 315 | | | | | 320 | |
| gcc | gag | tct | ccc | agg | atg | ctg | gac | cca | cag | acc | gag | gag | aaa | gag | gcc | 1008 |
| Ala | Glu | Ser | Pro | Arg | Met | Leu | Asp | Pro | Gln | Thr | Glu | Glu | Lys | Glu | Ala | |
| | | | | 325 | | | | | 330 | | | | | 335 | | |
| tct | ggg | gga | tcc | ctc | cag | ctt | ccc | cac | cag | ccc | ctc | caa | ggc | ggt | gat | 1056 |
| Ser | Gly | Gly | Ser | Leu | Gln | Leu | Pro | His | Gln | Pro | Leu | Gln | Gly | Gly | Asp | |
| | | | | 340 | | | | | 345 | | | | | 350 | | |
| gtg | gtc | aca | atc | ggg | ggc | ttc | acc | ttt | gtg | atg | aat | gac | cgc | tcc | tac | 1104 |
| Val | Val | Thr | Ile | Gly | Gly | Phe | Thr | Phe | Val | Met | Asn | Asp | Arg | Ser | Tyr | |
| | | | 355 | | | | | 360 | | | | | 365 | | | |
| gtg | gcg | ttg | gac | tac | aag | gac | gac | gat | gac | aag | tag | | | | | 1140 |
| Val | Ala | Leu | Asp | Tyr | Lys | Asp | Asp | Asp | Asp | Lys | | | | | | |
| | | | 370 | | | | | 375 | | | | | | | | |

```
<210> SEQ ID NO 8
<211> LENGTH: 379
<212> TYPE: PRT
<213> ORGANISM: Artificial Sequence
<220> FEATURE:
<223> OTHER INFORMATION: Synthetic Construct

<400> SEQUENCE: 8
```

| | | | | | | | | | | | | | | |
|---|---|---|---|---|---|---|---|---|---|---|---|---|---|---|
| Met | Gly | Arg | Leu | Val | Leu | Leu | Trp | Gly | Ala | Ala | Val | Phe | Leu | Leu | Gly |
| 1 | | | | 5 | | | | | 10 | | | | | 15 | |
| Gly | Trp | Met | Ala | Leu | Gly | Gln | Gly | Gly | Ala | Ala | Glu | Gly | Val | Gln | Ile |
| | | | 20 | | | | | 25 | | | | | 30 | | |
| Gln | Ile | Ile | Tyr | Phe | Asn | Leu | Glu | Thr | Val | Gln | Val | Thr | Trp | Asn | Ala |
| | | 35 | | | | | 40 | | | | | 45 | | | |
| Ser | Lys | Tyr | Ser | Arg | Thr | Asn | Leu | Thr | Phe | His | Tyr | Arg | Phe | Asn | Gly |
| | 50 | | | | | 55 | | | | | 60 | | | | |

Asp Glu Ala Tyr Asp Gln Cys Thr Asn Tyr Leu Leu Gln Glu Gly His
 65                  70                  75                  80

Thr Ser Gly Cys Leu Leu Asp Ala Glu Gln Arg Asp Asp Ile Leu Tyr
                 85                  90                  95

Phe Ser Ile Arg Asn Gly Thr His Pro Val Phe Thr Ala Ser Arg Trp
            100                 105                 110

Met Val Tyr Tyr Leu Lys Pro Ser Ser Pro Lys His Val Arg Phe Ser
        115                 120                 125

Trp His Gln Asp Ala Val Thr Val Thr Cys Ser Asp Leu Ser Tyr Gly
    130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Glu Val Thr Cys
        195                 200                 205

Trp Gln Arg Gly Glu Ile Arg Asp Ala Cys Ala Glu Thr Pro Thr Pro
    210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
                260                 265                 270

Pro Gly Leu Phe Glu Ile His Gln Gly Asn Phe Gln Glu Trp Ile Thr
            275                 280                 285

Asp Thr Gln Asn Val Ala His Leu His Lys Met Ala Gly Ala Glu Gln
        290                 295                 300

Glu Ser Gly Pro Glu Glu Pro Leu Val Val Gln Leu Ala Lys Thr Glu
305                 310                 315                 320

Ala Glu Ser Pro Arg Met Leu Asp Pro Gln Thr Glu Glu Lys Glu Ala
                325                 330                 335

Ser Gly Gly Ser Leu Gln Leu Pro His Gln Pro Leu Gln Gly Gly Asp
            340                 345                 350

Val Val Thr Ile Gly Gly Phe Thr Phe Val Met Asn Asp Arg Ser Tyr
        355                 360                 365

Val Ala Leu Asp Tyr Lys Asp Asp Asp Lys
    370                 375

<210> SEQ ID NO 9
<211> LENGTH: 357
<212> TYPE: PRT
<213> ORGANISM: Artificial Sequence
<220> FEATURE:
<223> OTHER INFORMATION: Description of Artificial Sequence: Human
      TSLPR-FLAG
<220> FEATURE:
<221> NAME/KEY: TRANSMEM
<222> LOCATION: (210)..(230)
<220> FEATURE:
<221> NAME/KEY: DOMAIN
<222> LOCATION: (350)..(357)
<223> OTHER INFORMATION: FLAG sequence

<400> SEQUENCE: 9

```
Gln Gly Gly Ala Ala Glu Gly Val Gln Ile Gln Ile Ile Tyr Phe Asn
1               5                   10                  15

Leu Glu Thr Val Gln Val Thr Trp Asn Ala Ser Lys Tyr Ser Arg Thr
            20                  25                  30

Asn Leu Thr Phe His Tyr Arg Phe Asn Gly Asp Glu Ala Tyr Asp Gln
                35                  40                  45

Cys Thr Asn Tyr Leu Leu Gln Glu Gly His Thr Ser Gly Cys Leu Leu
50                  55                  60

Asp Ala Glu Gln Arg Asp Ile Leu Tyr Phe Ser Ile Arg Asn Gly
65                  70                  75                  80

Thr His Pro Val Phe Thr Ala Ser Arg Trp Met Val Tyr Tyr Leu Lys
                85                  90                  95

Pro Ser Ser Pro Lys His Val Arg Phe Ser Trp His Gln Asp Ala Val
                100                 105                 110

Thr Val Thr Cys Ser Asp Leu Ser Tyr Gly Asp Leu Leu Tyr Glu Val
            115                 120                 125

Gln Tyr Arg Ser Pro Phe Asp Thr Glu Trp Gln Ser Lys Gln Glu Asn
            130                 135                 140

Thr Cys Asn Val Thr Ile Glu Gly Leu Asp Ala Glu Lys Cys Tyr Ser
145                 150                 155                 160

Phe Trp Val Arg Val Lys Ala Met Glu Asp Val Tyr Gly Pro Asp Thr
                165                 170                 175

Tyr Pro Ser Asp Trp Ser Glu Val Thr Cys Trp Gln Arg Gly Glu Ile
                180                 185                 190

Arg Asp Ala Cys Ala Glu Thr Pro Thr Pro Lys Pro Lys Leu Ser
                195                 200                 205

Lys Phe Ile Leu Ile Ser Ser Leu Ala Ile Leu Leu Met Val Ser Leu
210                 215                 220

Leu Leu Leu Ser Leu Trp Lys Leu Trp Arg Val Lys Lys Phe Leu Ile
225                 230                 235                 240

Pro Ser Val Pro Asp Pro Lys Ser Ile Phe Pro Gly Leu Phe Glu Ile
                245                 250                 255

His Gln Gly Asn Phe Gln Glu Trp Ile Thr Asp Thr Gln Asn Val Ala
                260                 265                 270

His Leu His Lys Met Ala Gly Ala Glu Gln Glu Ser Gly Pro Glu Glu
            275                 280                 285

Pro Leu Val Val Gln Leu Ala Lys Thr Glu Ala Glu Ser Pro Arg Met
            290                 295                 300

Leu Asp Pro Gln Thr Glu Glu Lys Glu Ala Ser Gly Gly Ser Leu Gln
305                 310                 315                 320

Leu Pro His Gln Pro Leu Gln Gly Gly Asp Val Val Thr Ile Gly Gly
                325                 330                 335

Phe Thr Phe Val Met Asn Asp Arg Ser Tyr Val Ala Leu Asp Tyr Lys
                340                 345                 350

Asp Asp Asp Asp Lys
            355
```

<210> SEQ ID NO 10
<211> LENGTH: 1379
<212> TYPE: DNA
<213> ORGANISM: Artificial Sequence
<220> FEATURE:
<223> OTHER INFORMATION: Description of Artificial Sequence: Clone
      9604927 containing human TSLPR sequence
<220> FEATURE:
<221> NAME/KEY: misc_feature
<222> LOCATION: (1)..(68)
<223> OTHER INFORMATION: Vector sequence
<220> FEATURE:
<221> NAME/KEY: sig_peptide
<222> LOCATION: (70)..(135)
<220> FEATURE:
<221> NAME/KEY: misc_feature
<222> LOCATION: (763)..(825)
<223> OTHER INFORMATION: Predicted transmembrane domain coding sequence
<220> FEATURE:
<221> NAME/KEY: misc_feature
<222> LOCATION: (1186)..(1379)
<223> OTHER INFORMATION: Vector sequence

<400> SEQUENCE: 10

```
ggatccacta gtaacggccg ccagtgtgct ggaattctgc agatatccat cacactggcg      60
gccgccacca tggggcggct ggttctgctg tggggagctg ccgtctttct gctggggagc     120
tggatggctt tggggcaagg aggagcagca gaaggagtac agattcagat catctacttc     180
aatttagaaa ccgtgcaggt gacatggaat gccagcaaat actccaggac caacctgact     240
ttccactaca gattcaacgg tgatgaggcc tatgaccagt gcaccaacta ccttctccag     300
gaaggtcaca cttcagggtg cctcctagac gcagagcagc gagacgacat tctctatttc     360
tccatcagga atgggacgca ccccgttttc accgcaagtc gctggatggt ttattacctg     420
aaacccagtt ccccgaagca cgtgagattt tcgtggcatc aggatgcagt gacggtgacg     480
tgttctgacc tgtcctacgg ggatctcctc tatgaggttc agtaccggag ccccttcgac     540
accgagtggc agtccaaaca ggaaaatacc tgcaacgtca ccatagaagg cttggatgcc     600
gagaagtgtt actctttctg ggtcagggtg aaggctatgg aggatgtata tgggccagac     660
acatacccaa gcgactggtc agaggtgaca tgctggcaga gaggcgagat cgggatgcc      720
tgtgcagaga caccaacgcc tcccaaacca agctgtcca aatttatttt aatttccagc     780
ctggccatcc ttctgatggt gtctctcctc cttctgtctt tatggaaatt atggagagtg     840
aagaagtttc tcattcccag cgtgccagac ccgaaatcca tcttccccgg gctctttgag     900
atacaccaag ggaacttcca ggagtggatc acagacaccc agaacgtggc ccacctccac     960
aagatggcag gtgcagagca agaaagtggc ccctgaggagc ccctggtagt ccagttggcc    1020
aagactgaag ccgagtctcc caggatgctg gacccacaga ccgaggagaa agaggcctct    1080
gggggatccc tccagcttcc ccaccagccc tccaaggcg gtgatgtggt cacaatcggg    1140
ggcttcacct ttgtgatgaa tgaccgctcc tacgtggcgt tgtgatctaa agggccctat    1200
tctatactgt cacctaaatg ctagagctcg ctgatcagcc tcgactgtgc cttctagttg    1260
ccagccatct gttgtttgcc cctccccgt gccttccttg accctggaat gtgccactcc    1320
cactgtcctt tcctaataaa atgaagaaat tgcatccgca ttgtctgagt aggtgtcta    1379
```

<210> SEQ ID NO 11
<211> LENGTH: 1415
<212> TYPE: DNA
<213> ORGANISM: Artificial Sequence
<220> FEATURE:
<223> OTHER INFORMATION: Description of Artificial Sequence: Clone 9508990 containing human TSLPR-FLAG sequence
<220> FEATURE:
<221> NAME/KEY: misc_feature
<222> LOCATION: (1)..(60)
<223> OTHER INFORMATION: Vector sequence
<220> FEATURE:
<221> NAME/KEY: sig_peptide
<222> LOCATION: (62)..(127)
<220> FEATURE:
<221> NAME/KEY: misc_feature

```
<222> LOCATION: (755)..(817)
<223> OTHER INFORMATION: Predicted transmembrane domain coding sequence
<220> FEATURE:
<221> NAME/KEY: misc_feature
<222> LOCATION: (1175)..(1201)
<223> OTHER INFORMATION: FLAG coding sequence
<220> FEATURE:
<221> NAME/KEY: misc_feature
<222> LOCATION: (1202)..(1415)
<223> OTHER INFORMATION: Vector sequence

<400> SEQUENCE: 11
ggatccacta gtaacggccg ccagtgtgct ggaattctgc agatatccat cacactggcc      60
catgggcgg  ctggttctgc tgtggggagc tgccgtcttt ctgctgggag ctggatggc     120
tttgggcaa  ggaggagcag cagaaggagt acagattcag atcatctact tcaatttaga    180
aaccgtgcag gtgacatgga atgccagcaa atactccagg accaacctga ctttccacta    240
cagattcaac ggtgatgagg cctatgacca gtgcaccaac taccttctcc aggaaggtca    300
cacttcaggg tgcctcctag acgcagagca gcgagacgac attctctatt tctccatcag    360
gaatgggacg cacccgtttt caccgcaag  tcgctggatg gtttattacc tgaaacccag    420
ttccccgaag cacgtgagat tttcgtggca tcaggatgca gtgacggtga cgtgttctga    480
cctgtcctac ggggatctcc tctatgaggt tcagtaccgg agccccttcg acaccgagtg    540
gcagtccaaa caggaaaata cctgcaacgt caccatagaa ggcttggatg ccgagaagtg    600
ttactctttc tgggtcaggg tgaaggctat ggaggatgta tatgggccag acacataccc    660
aagcgactgg tcagaggtga catgctggca gagaggcgag attcgggatg cctgtgcaga    720
gacaccaacg cctcccaaac caaagctgtc caaatttatt ttaatttcca gcctggccat    780
ccttctgatg gtgtctctcc tccttctgtc tttatggaaa ttatggagag tgaagaagtt    840
tctcattccc agcgtgccag acccgaaatc catcttcccc gggctctttg agatacacca    900
agggaacttc caggagtgga tcacagacac ccagaacgtg gcccacctcc acaagatggc    960
aggtgcagag caagaaagtg gccccgagga gcccctggta gtccagttgg ccaagactga   1020
agccgagtct cccaggatgc tggacccaca gaccgaggag aaagaggcct ctggggatc    1080
cctccagctt ccccaccagc ccctccaagg cggtgatgtg gtcacaatcg ggggcttcac   1140
ctttgtgatg aatgaccgct cctacgtggc gttggactac aaggacgacg atgacaagta   1200
gtctagaggg cccctattcta tagtgtcacc taaatgctag agctcgctga tcagactcga   1260
ctgtgccttc tagttgccag ccatctgttg tttgcccctc cccgtgcctt ccttgaccc     1320
tggaaggtgc cactcccact gtcctttcct aataaaatga ggaaattgca tcgcattgtc   1380
tgagtaggtg tcattctatt ctgggggtg gcgtt                               1415

<210> SEQ ID NO 12
<211> LENGTH: 369
<212> TYPE: PRT
<213> ORGANISM: Mus musculus

<400> SEQUENCE: 12

Met Leu Lys Leu Leu Leu Ser Pro Arg Ser Phe Leu Val Leu Gln Leu
1               5                   10                  15

Leu Leu Leu Arg Ala Gly Trp Ser Ser Lys Val Leu Met Ser Ser Ala
                20                  25                  30

Asn Glu Asp Ile Lys Ala Asp Leu Ile Leu Thr Ser Thr Ala Pro Glu
            35                  40                  45

His Leu Ser Ala Pro Thr Leu Pro Leu Pro Glu Val Gln Cys Phe Val
```

```
                50                  55                  60
Phe Asn Ile Glu Tyr Met Asn Cys Thr Trp Asn Ser Ser Glu Pro
 65                  70                  75                  80

Gln Ala Thr Asn Leu Thr Leu His Tyr Arg Tyr Lys Val Ser Asp Asn
                 85                  90                  95

Asn Thr Phe Gln Glu Cys Ser His Tyr Leu Phe Ser Lys Glu Ile Thr
                100                 105                 110

Ser Gly Cys Gln Ile Gln Lys Glu Asp Ile Gln Leu Tyr Gln Thr Phe
                115                 120                 125

Val Val Gln Leu Gln Asp Pro Gln Lys Pro Gln Arg Arg Ala Val Gln
            130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
                165                 170                 175

Arg His Ile Lys Glu Arg Cys Leu Gln Tyr Leu Val Gln Tyr Arg Ser
                180                 185                 190

Asn Arg Asp Arg Ser Trp Thr Glu Leu Ile Val Asn His Glu Pro Arg
            195                 200                 205

Phe Ser Leu Pro Ser Val Asp Glu Leu Lys Arg Tyr Thr Phe Arg Val
210                 215                 220

Arg Ser Arg Tyr Asn Pro Ile Cys Gly Ser Ser Gln Gln Trp Ser Lys
225                 230                 235                 240

Trp Ser Gln Pro Val His Trp Gly Ser His Thr Val Glu Glu Asn Pro
                245                 250                 255

Ser Leu Phe Ala Leu Glu Ala Val Leu Ile Pro Val Gly Thr Met Gly
                260                 265                 270

Leu Ile Ile Thr Leu Ile Phe Val Tyr Cys Trp Leu Glu Arg Met Pro
                275                 280                 285

Pro Ile Pro Pro Ile Lys Asn Leu Glu Asp Leu Val Thr Glu Tyr Gln
            290                 295                 300

Gly Asn Phe Ser Ala Trp Ser Gly Val Ser Lys Gly Leu Thr Glu Ser
305                 310                 315                 320

Leu Gln Pro Asp Tyr Ser Glu Arg Phe Cys His Val Ser Glu Ile Pro
                325                 330                 335

Pro Lys Gly Gly Ala Leu Gly Glu Gly Pro Gly Ser Pro Cys Ser
            340                 345                 350

Leu His Ser Pro Tyr Trp Pro Pro Cys Tyr Ser Leu Lys Pro Glu
                355                 360                 365

Ala
```

<210> SEQ ID NO 13
<211> LENGTH: 11
<212> TYPE: PRT
<213> ORGANISM: Human immunodeficiency virus type 1

<400> SEQUENCE: 13

```
Tyr Gly Arg Lys Lys Arg Arg Gln Arg Arg Arg
 1               5                  10
```

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:

```
      Internalizing domain derived from HIV tat protein

<400> SEQUENCE: 14

Gly Gly Gly Gly Tyr Gly Arg Lys Lys Arg Arg Gln Arg Arg Arg
1               5                  10                  15

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Type I
      cytokine receptor conserved motif
<220> FEATURE:
<221> NAME/KEY: UNSURE
<222> LOCATION: (3)..(3)
<223> OTHER INFORMATION: Xaa can be any naturally occurring amino acid

<400> SEQUENCE: 15

Trp Ser Xaa Trp Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Motif
      replacing type I cytokine receptor conserved motif in murine TSLPR
      polypeptide

<400> SEQUENCE: 16

Trp Thr Ala Val Thr
1               5
```